(12) United States Patent
Schmitt

(10) Patent No.: US 7,916,387 B2
(45) Date of Patent: Mar. 29, 2011

(54) METHODS AND APPARATUS FOR SWEPT-SOURCE OPTICAL COHERENCE TOMOGRAPHY

(75) Inventor: Joseph M. Schmitt, Andover, MA (US)

(73) Assignee: LightLab Imaging, Inc., Westford, MA (US)

(*) Notice: Subject to any disclaimer, the term of this patent is extended or adjusted under 35 U.S.C. 154(b) by 490 days.

(21) Appl. No.: 12/008,403

(22) Filed: Jan. 10, 2008

(65) Prior Publication Data
US 2008/0165366 A1 Jul. 10, 2008

Related U.S. Application Data

(60) Provisional application No. 60/879,880, filed on Jan. 10, 2007.

(51) Int. Cl.
*H01S 5/00* (2006.01)
*H01S 3/098* (2006.01)

(52) U.S. Cl. .................. 359/344; 372/18; 372/20

(58) Field of Classification Search ............ 372/18, 372/20; 359/344
See application file for complete search history.

(56) References Cited

U.S. PATENT DOCUMENTS

| | | | |
|---|---|---|---|
| 5,321,501 A | 6/1994 | Swanson et al. | |
| 5,459,570 A | 10/1995 | Swanson | |
| 5,465,147 A | 11/1995 | Swanson | |
| 5,509,093 A | 4/1996 | Miller et al. | |
| 5,748,598 A | 5/1998 | Swanson et al. | |
| 5,784,352 A | 7/1998 | Swanson et al. | |
| 5,956,355 A * | 9/1999 | Swanson et al. | ............ 372/20 |
| 6,111,645 A | 8/2000 | Tearney et al. | |
| 6,134,003 A | 10/2000 | Tearney et al. | |
| 6,160,826 A | 12/2000 | Swanson et al. | |
| 6,191,862 B1 | 2/2001 | Swanson et al. | |
| 6,282,011 B1 | 8/2001 | Tearney et al. | |
| 6,421,164 B2 | 7/2002 | Tearney et al. | |
| 6,445,939 B1 | 9/2002 | Swanson et al. | |
| 6,485,413 B1 | 11/2002 | Boppart | |
| 6,501,551 B1 | 12/2002 | Tearney et al. | |
| 6,552,796 B2 | 4/2003 | Magnin et al. | |
| 6,564,087 B1 | 5/2003 | Pitris et al. | |

(Continued)

FOREIGN PATENT DOCUMENTS

| | | |
|---|---|---|
| WO | 2005/047813 A1 | 5/2005 |
| WO | 2006/130802 A2 | 12/2006 |

OTHER PUBLICATIONS

Chinn SR, Swanson EA, and Fujimoto JG, "Optical coherence tomography using a frequency-tunable optical source," Opt. Lett., vol. 22, 340-342 (1997).

(Continued)

*Primary Examiner* — Eric Bolda
(74) *Attorney, Agent, or Firm* — K&L Gates LLP

(57) ABSTRACT

In one embodiment of the invention, a semiconductor optical amplifier (SOA) in a laser ring is chosen to provide low polarization-dependent gain (PDG) and a booster semiconductor optical amplifier, outside of the ring, is chosen to provide high polarization-dependent gain. The use of a semiconductor optical amplifier with low polarization-dependent gain nearly eliminates variations in the polarization state of the light at the output of the laser, but does not eliminate the intra-sweep variations in the polarization state at the output of the laser, which can degrade the performance of the SS-OCT system.

21 Claims, 18 Drawing Sheets

U.S. PATENT DOCUMENTS

| | | |
|---|---|---|
| 6,570,659 B2 | 5/2003 | Schmitt |
| 6,879,851 B2 | 4/2005 | McNamara et al. |
| 6,891,984 B2 | 5/2005 | Petersen et al. |
| 7,208,333 B2 | 4/2007 | Flanders et al. |
| 7,241,286 B2 | 7/2007 | Atlas |
| 7,414,779 B2 | 8/2008 | Huber et al. |
| 7,415,049 B2 | 8/2008 | Flanders et al. |
| 2004/0215166 A1 | 10/2004 | Atlas |
| 2005/0201662 A1 | 9/2005 | Petersen et al. |
| 2005/0238067 A1 | 10/2005 | Choi |
| 2006/0095065 A1 | 5/2006 | Tanimura et al. |
| 2006/0187537 A1* | 8/2006 | Huber et al. ............. 359/337.22 |
| 2006/0203859 A1 | 9/2006 | Cable et al. |
| 2006/0241503 A1 | 10/2006 | Schmitt et al. |
| 2006/0244973 A1 | 11/2006 | Yun et al. |
| 2007/0260198 A1 | 11/2007 | Atlas |
| 2008/0161696 A1 | 7/2008 | Schmitt et al. |
| 2008/0165366 A1 | 7/2008 | Schmitt et al. |

OTHER PUBLICATIONS

Choma MA, Satanic MV, Yang C, and Izatt J, "Sensitivity advantage of swept source and Fourier domain optical coherence tomography," Opt. Express, vol. 11, 2183-2189 (2003).

Choma MA, Hsu K, and Izatt J," Swept source optical coherence tomography using an all-fiber 1300 nm ring laser source," J. Biomed. Optics, vol. 10, p. 044009 (2005).

Huang, David, et al., "Optical Coherence Tomography," Science, vol. 254, 1991, pp. 1178-1181.

Huber R, Wojtkowski, Taira K, Fujimoto JG, and Hsu K, "Amplified, frequency-swept lasers for frequency domain reflectometry and OCT imaging: design and scaling principles," Opt. Express, vol. 13, 3513-3528 (2005).

Huber R, Wojtkowski M, and Fujimoto JG, "Fourier Domain Mode Locking (FDML): A new laser operating regime and applications for optical coherence tomography," Optics Express, vol. 14, pp. 3225-3237 (2006).

Yun Sh, Tearney GJ, Bouma BE, Park BH, de Boer JF, "High-speed spectral domain optical coherence tomography at 1.3 mm wavelength," Optics Express, vol. 11, pp. 3598-3604 (2003).

International Search Report and Written Opinion of the International Searching Authority for International Application No. PCT/US2008/000341, mailed Jun. 25, 2008 (12 pgs.).

* cited by examiner

METHODS AND APPARATUS FOR SWEPT-SOURCE OPTICAL COHERENCE TOMOGRAPHY

RELATED APPLICATIONS

This application claims priority to U.S. Provisional Patent Application 60/879,880 filed on Jan. 10, 2007, the disclosure of which is herein incorporated by reference in its entirety.

FIELD OF INVENTION

This invention relates to the field of optical imaging and more specifically to the design and implementation of optical coherence tomography (OCT) systems that employ swept-frequency lasers as light sources.

BACKGROUND

Optical coherence tomography (OCT) is an interferometric imaging technique with widespread applications in ophthalmology, cardiology, gastroenterology and other fields of medicine. Huang D, Swanson E A, Lin C P, Schuman J S, Stinson W G, Chang W, Hee M R, Flotte T, Gregory K, Puliafito C A, and Fujimoto J G, "Optical coherence tomography," *Science*, Vol 254, 1178-1181 (1991). The ability to view subsurface structures with high resolution (2-15 μm) through small-diameter fiber-optic probes makes OCT especially useful for minimally invasive imaging of internal tissues and organs. Commercially available time-domain OCT systems do not provide sufficient scan speed for unimpeded real-time visualization of organs that move rapidly or that have large surface areas. In the beating heart, for example, OCT imaging of the coronary arteries is a challenge, because imaging must be performed rapidly enough to allow clear visualization of a long segment (>3 cm) of an artery within the interval during which blood is cleared from the field of the view of the probe. The image acquisition rate of the current generation of commercially available OCT systems for coronary artery imaging is limited to approximately 15 images/sec. At this acquisition speed, occlusion of the blood flow with a balloon for at least 30 seconds is required to image a 3-cm segment of the target artery. If the image acquisition rate of OCT systems could be increased by at least an order of magnitude, without significant loss of image quality, balloon occlusion of long periods could be avoided. A segment of an artery could then be imaged by simply injecting a bolus of saline over a few seconds, thereby simplifying the imaging procedure while reducing the risk of myocardial ischemia.

Time-domain OCT systems employ a broadband light source as an input to an interferometer with a mechanically actuated reference arm for path-length scanning. The interference signals generated by reflections from structures at different depths are measured point-by-point as the reference path length changes. In this measurement scheme, the maximum scanning speed is limited both by the dynamic mechanical constraints of the actuator and by the spectral power density of the light source. In such a system using a superluminescent light source that emits an output power of 25 mW over a spectral bandwidth of 40-60 nm, the maximum depth-scanning velocity that can be achieved while maintaining an adequate signal-to-noise ratio for tissue imaging (>90 dB) is approximately 25 m/s. Therefore, 512-line images of a 5 mm deep object can be acquired at a rate no greater than 10 per second.

Frequency-domain (also called Fourier-domain) (FD) OCT overcomes these speed constraints by taking advantage of optical frequency discrimination methods based on Fourier transformation, which eliminate the need for long-range mechanical actuators. Swanson E A and Chinn S R, "Method and Apparatus for Performing Optical Frequency Domain Reflectometry" U.S. Pat. No. 6,160,826 (issued Dec. 12, 2000); Choma M A, Sarunic M V, Yang C, and Izatt J, "Sensitivity advantage of swept source and Fourier domain optical coherence tomography," *Opt. Express*, Vol. 11, 2183-2189 (2003). Instead of wasting available source power by interrogating the sample point-by-point, FD-OCT collects information from multiple depths simultaneously and discriminates reflections from different depths according to the optical frequencies of the signals they generate. FD-OCT imaging can be accomplished by illuminating the sample with a broadband source and dispersing the reflected light with a spectrometer onto an array detector. Alternatively, the sample can be illuminated with a rapid wavelength-tuned laser and the light reflected during a wavelength sweep collected with a single photodetector. In both cases, a profile of reflections from different depths is obtained by Fourier transformation of the recorded interference signals. Because of their potential to achieve higher performance at lower cost in the 1300 nm spectral region, FD-OCT systems based on swept-frequency laser sources have attracted the most attention for medical applications that require subsurface imaging in highly scattering tissues.

The feasibility of swept-source OCT (SS-OCT) has been demonstrated in several academic research studies. Chinn S R, Swanson E A, and Fujimoto J G, "Optical coherence tomography using a frequency-tunable optical source," *Opt. Lett.*, Vol. 22, 340-342 (1997); Yun S H, Tearney G J, Bouma B E, Park B H, de Boer J F, "High-speed spectral domain optical coherence tomography at 1.3 μm wavelength," *Optics Express*, Vol. 11, pp. 3598-3604 (2003); Choma M A, Hsu K, and Izatt J, "Swept source optical coherence tomography using an all-fiber 1300 nm ring laser source," *J. Biomed. Optics*, Vol. 10, p. 044009 (2005); Huber R, Wojtkowski, Taira K, Fujimoto J G, and Hsu K, "Amplified, frequency-swept lasers for frequency domain reflectometry and OCT imaging: design and scaling principles," *Opt. Express*, Vol. 13, 3513-3528 (2005). Most of the reported SS-OCT systems employ short-cavity lasers tuned rapidly by an electronically actuated Fabry-Perot filter or a motor-driven grating filter. The implementations disclosed to date suffer from drawbacks that discourage widespread commercialization of SS-OCT. Specifically, current implementations make real-time data acquisition and display difficult, because they employ data acquisition schemes that require post-acquisition re-sampling or interpolation of recorded data before Fourier transformation. In addition, the relatively short coherence length and tendency for mode-hopping of short-cavity lasers reduce signal-to-noise and image resolution at optical scan depths exceeding 2-3 mm. Many medical applications, including coronary artery imaging, require an optical scan depth that exceeds 5 mm.

The recent development of Fourier-Domain Mode Locking (FDML) solves the problem of degraded signal-to-noise and image resolution at large optical scan depths. Huber R, Taira K, and Fujimoto J, "Mode Locking Methods and Apparatus," U.S. Patent Application No. 2006/0187537, (Published Aug. 24, 2006); Huber R, Wojtkowski M, and Fujimoro J G, "Fourier Domain Mode Locking (FDML): A new laser operating regime and applications for optical coherence tomography," *Optics Express*, Vol. 14, pp. 3225-3237 (2006). However, the practical implementation of a FDML-based SS-OCT system presents several technical challenges. The present invention addresses these challenges and provides solutions to the same.

SUMMARY OF THE INVENTION

The present invention describes devices and methods that enable stable, low-noise, and efficient operation of swept-source OCT (SS-OCT) systems at high speed, with continuous real-time image display. The methods detailed herein overcome disadvantages of previous implementations of SS-OCT systems, which include poor noise performance, limited scan range, the effects the birefringence and dispersion properties of the laser cavity, phase jitter, and sampling speed limitations.

In one aspect, the invention relates to an optical coherence tomography data collection apparatus. The apparatus can include a first gain element, a second gain element, where each gain element has a different gain dependence on polarization, and a Fourier-domain mode-locked laser defining a cavity. The laser can include a frequency tuning element in optical communication with the first gain element, where the first gain element can be disposed within the laser cavity and the second gain element can be disposed outside the cavity, and the gain dependence on polarization of the first gain element is less than the gain dependence on polarization of the second gain element.

The apparatus can include a sample clock generator, where the sample clock generator can be configured to clock an analog-to-digital converter. The analog-to-digital converter can be configured to sample interference signals at an output of a main interferometer. The apparatus can include a digital control system configured to stabilize a drive frequency of the frequency tuning element of the Fourier-domain mode-locked laser using at least one control signal derived from the sample clock generator. The Fourier-domain mode-locked laser can include an optical delay element that includes a pair of fiber coils whose relative orientations are adjusted to reduce the effects of polarization mode dispersion.

The sample clock generator can include a sample clock interferometer, a photoreceiver, an automatic gain control amplifier, a frequency multiplier, a zero-crossing detector, and/or a clock switch. The sample clock generator can include a Mach-Zehnder interferometer, including a pair of 2×2 fiber couplers, a Michelson interferometer with mismatched lengths in sample and reference arms, a common-path Michelson interferometer, including an element with two partially reflective interfaces, and/or a Fabry-Perot interferometer. The sample clock generator can include an analog multiplier. The analog multiplier can be configured to perform a squaring function on an input interference signal. The sample clock generator can include an analog multiplier for the multiplication of a pair of signals derived from an interference signal transmitted through a phase-shifting RF power splitter. The sample clock generator can include an exclusive OR gate for the transmission of a pair of phase-shifted pulse trains, the pulse trains derived from a zero-crossing detector applied to an interference signal, and a delayed replica of the zero-crossing detector's output. The sample clock generator can include an exclusive OR gate for the transmission of a pair of phase-shifted pulse trains, wherein the pulse trains are derived from a pair of zero-crossing detectors applied to sinusoidal signals derived from a phase-shifting power splitter.

The sample clock interferometer can generate phase-shifted interference signals for frequency modulation from a combination of a 2×2 coupler and a 3×3 coupler. The power splitting ratio of the 3×3 coupler can be chosen to obtain a pair of interference signals whose phases differ by approximately 90 degrees. The sample clock interferometer can generate phase-shifted interference signals for frequency modulation from a combination of a 2×2 coupler and a 3×3 coupler, the power splitting ratio of the 3×3 coupler chosen to obtain a pair of interference signals whose phases differ by approximately 90 degrees. The apparatus can further include a 4×4 coupler, the 4×4 coupler generating a pair of balanced signals with a quadrature phase relationship, the sample clock generator generating a single ADC clock signal. The sample clock generator can generate complex-valued signals for Fourier transformation by recording OCT data using a pair of ADC clock signals whose phases differ by 90 degrees.

In one aspect, the invention relates to a method of OCT imaging. The method can include generating light from a Fourier-domain mode-locked laser, where the laser can define a cavity and include a first gain element, and the first gain element can be disposed within the laser cavity. The method can include transmitting the generated light through a second gain element, where the second gain element can be disposed outside the cavity and each gain element can have a different gain dependence on polarization. The gain dependence on polarization of the first gain element can be less than the gain dependence on polarization of the second gain element. The method can include sampling interference signals at an output of a main interferometer using an analog-to-digital converter. The analog-to-digital converter can be clocked using a sample clock generator. The method can include optimizing a drive frequency of a frequency tuning element of the laser with a digital control system, where at least one control signal derived from the sample clock generator.

The method can further include the step of generating a pair of balanced signals with a quadrature phase relationship for dual-channel acquisition of OCT signals from the main interferometer using a 4×4 coupler, whereby only a single ADC clock signal from the sample clock generator is required. The step of optimizing the drive frequency can include measuring the instantaneous RMS amplitude $\Phi(t)$ of the interference signal at the output of the sample clock interferometer's photoreceiver at the time $\tau$ indicated by transmission of a pulse through a fiber-Bragg filter with a narrow passband in the vicinity of the zero-dispersion wavelength of the optical delay element and adjusting the frequency of a direct digital synthesis (DDS) generator to maximize the value of $\Phi(t)$.

The step of optimizing the drive frequency can include measuring the desired delay D between zero-crossing times of a drive waveform and an initial laser sweep and adjusting a dc bias with a digital-to-analog converter to maintain a fixed delay $\tau$–D, where $\tau$ is the time measured by transmission of the pulse through a fiber-Bragg filter with a narrow passband in the vicinity of the zero-dispersion wavelength of the optical delay element.

In another aspect, the invention relates to an optical coherence tomography data collection apparatus, the apparatus includes an interferometer having an input and an output, an analog-to-digital converter configured to sample interference signals from the output, a first gain element, a second gain element, where each gain element can have a different gain dependence on polarization, a Fourier-domain mode-locked laser having a laser cavity, where the laser can be in optical communication with the interferometer. The laser can include a frequency tuning element in optical communication with the first gain element, the first gain element disposed within the laser cavity, the second gain element disposed outside the cavity, a sample clock generator configured to clock an analog-to-digital converter, and a digital control system configured to stabilize a drive frequency of the frequency tuning element of the laser, using a control signal derived from the sample clock generator. The gain dependence on polarization of the first gain element can be less than the gain dependence on polarization of the second gain element. The laser can include an optical delay element that includes a pair of fiber coils whose relative orientations are adjusted to reduce the effects of polarization mode dispersion.

The sample clock generator can include a sample clock interferometer, a photoreceiver, an automatic gain control amplifier, an optional frequency multiplier, a zero-crossing detector, and/or a clock switch. The sample clock generator can include an analog multiplier, where the analog multiplier can be configured to perform a squaring function on an input interference signal.

In one aspect, the invention relates to a method of increasing a useful duty cycle of a tuning element in a cavity of a FDML laser. The method includes the steps of linearizing a portion of a frequency tuning element duty cycle and driving a filter. The filter combines a plurality of phase-locked sine waves having a harmonic frequency relation, each wave having an adjustable amplitude and phase. In one embodiment, two of the plurality of sine waves having frequencies $f$ and $2f$ are generated by a pair of phase-locked digital-direct synthesis integrated circuits and whose weighted sum yields a smoothed ramp-like displacement of a piezo-electric or micro-electromechanical systems (MEMs) Fabry-Perot tunable filter. In another embodiment, two of the plurality of sine waves having frequencies $f$ and $3f$ are generated by a pair of phase-locked digital-direct synthesis integrated circuits and whose weighted sum yields a triangular-wave displacement of a piezo-electric or micro-electromechanical systems (MEMs) Fabry-Perot tunable filter.

In one embodiment of the invention, a semiconductor optical amplifier (SOA) in a laser ring is chosen to provide low polarization-dependent gain (PDG) and a booster semiconductor optical amplifier, outside of the ring, is chosen to provide high polarization-dependent gain. The use of a semiconductor optical amplifier with low polarization-dependent gain nearly eliminates variations in the polarization state of the light at the output of the laser, but does not eliminate the intra-sweep variations in the polarization state at the output of the laser, which can degrade the performance of the SS-OCT system. Some of the embodiments disclosed herein overcome variations in both the amplitude and polarization, because the booster semiconductor optical amplifier provides sufficient amplification in a single polarization axis to reach gain saturation at all wavelengths, in spite of the polarization variations at the output of the low polarization-dependent gain ring semiconductor optical amplifier.

One objective of this invention is to present methods for stabilization of the polarization state of light circulating within the long-path ring cavity of an FDML laser. These methods improve the performance and manufacturability of SS-OCT systems based on the FDML principle.

Another objective of the present invention is to describe opto-electronic methods and devices for generating a stable sample clock for direct acquisition of interferometric systems from various types of SS-OCT systems. These methods reduce phase noise, expand the dynamic range, and increase the acquisition speed of the acquired interference signals.

A further objective of the present invention is to disclose methods and devices for feedback stabilization of FDML SS-OCT systems. A practical embodiment is presented that includes a frequency-agile, direct digital synthesis (DDS) waveform generator and a digital microcontroller configured for optimization of an electronic feedback variable. A companion method for stabilization of the starting wavelength of the wavelength sweep of the FDML laser is also disclosed.

A still further objective of the present invention is to disclose methods for linearizing and extending the duty cycle of the optical frequency sweep of tunable lasers. These methods, which operate at high scan repetition rates, can be applied to piezoelectric and microelectromechanical (MEMs) actuators, including, but not limited to actuators with highly resonant mechanical properties.

Another further objective of the present invention is to reduce foldover artifacts. In one embodiment, a foldover artifact occurs when a sample portion under investigation is projected upon an opposing side of the sample portion to result in ambiguities in any resultant image. As used herein, a foldover artifact also refers to any phase wrapping, wrap around, or aliasing based ambiguities associated with OCT data capture.

The methods and systems are explained through the following description, drawings, and claims.

BRIEF DESCRIPTION OF THE DRAWINGS

The objects and features of the invention can be understood more completely by referring to the drawings described below and the accompanying descriptions. The drawings are not necessarily to scale, emphasis instead generally being placed upon illustrating the principles of the invention. In the drawings, like numerals are used to indicate like parts throughout the various views.

DETAILED DESCRIPTION

Figure 1:
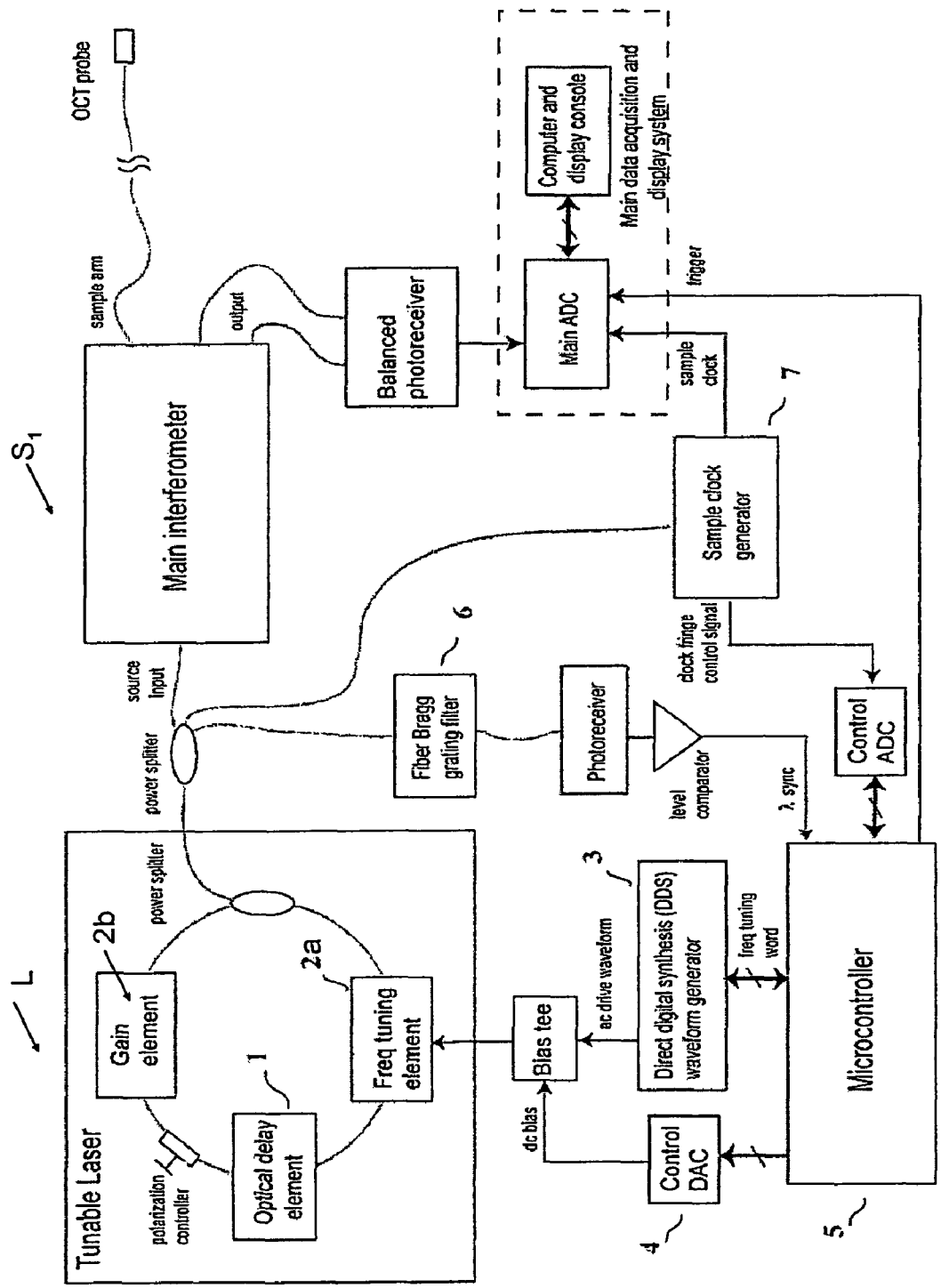
FIG. 1 is a block diagram of an SS-OCT system according to an illustrative embodiment of the invention.

The following description refers to the accompanying drawings that illustrate certain embodiments of the invention. Other embodiments are possible and modifications may be made to the embodiments without departing from the spirit and scope of the invention. Therefore, the following detailed description is not meant to limit the invention. Rather, the scope of the invention is defined by the appended claims.

In general, the invention relates to apparatus and methods for enhanced swept-source OCT system suitable for imaging various structures, such as those in a cadaver or living organism. Typically, these systems are based on a Fourier-Domain Mode Locking (FDML) approach. Using Fourier-Domain Mode Locking (FDML) when implementing the systems and methods described herein solves the problem of degraded signal-to-noise ratio and image resolution at large optical scan depths. However, the practical implementation of an FDML-based SS-OCT system presents several technical challenges.

First, to ensure stable and low-noise operation of an FDML-based SS-OCT system, the effects of the birefringence and dispersion properties of the laser cavity must be minimized. Second, to maintain the frequency-mode-locked condition, the period of the waveform that drives the tunable filter must have extremely low-phase jitter and must be matched precisely to the round-trip delay through the laser cavity. If the period of the drive waveform and round-trip delay differ by more than a small fraction (e.g., 10 ppm), the coherence and noise properties of the laser degrade markedly.

Moreover, to compensate for environmental influences, the period of the drive waveform must change in response to changes in the length of the cavity. Third, to ensure repeatable phase and amplitude characteristics of the acquired interference signals, the wavelength from which the wavelength sweep starts must be kept the same from sweep to sweep. Fourth, to enable real-time operation a FDML laser, configured to produce an output with high resolution, the interference signals must be sampled at high speed at precise optical-frequency intervals.

Aspects of the invention describe devices and methods that address the problems identified above by incorporating specific components in and adjusting the overall configuration of various FDML-based SS-OCT systems. Accordingly, the methods and apparatus described herein enable stable, low-noise, and efficient operation of swept-source OCT systems at high speed, with continuous real-time image display. The methods detailed herein overcome disadvantages of previous implementations of SS-OCT systems, which include high system cost and complexity, poor noise performance, and limited scan range.

In particular, since one or more long optical fiber loops are used in some of the systems disclosed herein to match the travel time in an optical circuit with the switching time of an electric circuit, environmental influences such as temperature variations and mechanical stress can introduce unwanted polarization effects in the optical fiber loops. In part, the embodiments disclosed herein overcome variations in both the amplitude and polarization, through implementation of booster semiconductor optical amplifiers to provide sufficient amplification in a single polarization axis to reach gain saturation at all wavelengths, in spite of the polarization variations at the output of the low polarization-dependent gain ring semiconductor optical amplifier. Thus, the presence of the semiconductor optical amplifiers address the problems introduced by providing long runs of optical fiber to match optical travel and electronic switching times.

Figure 2:
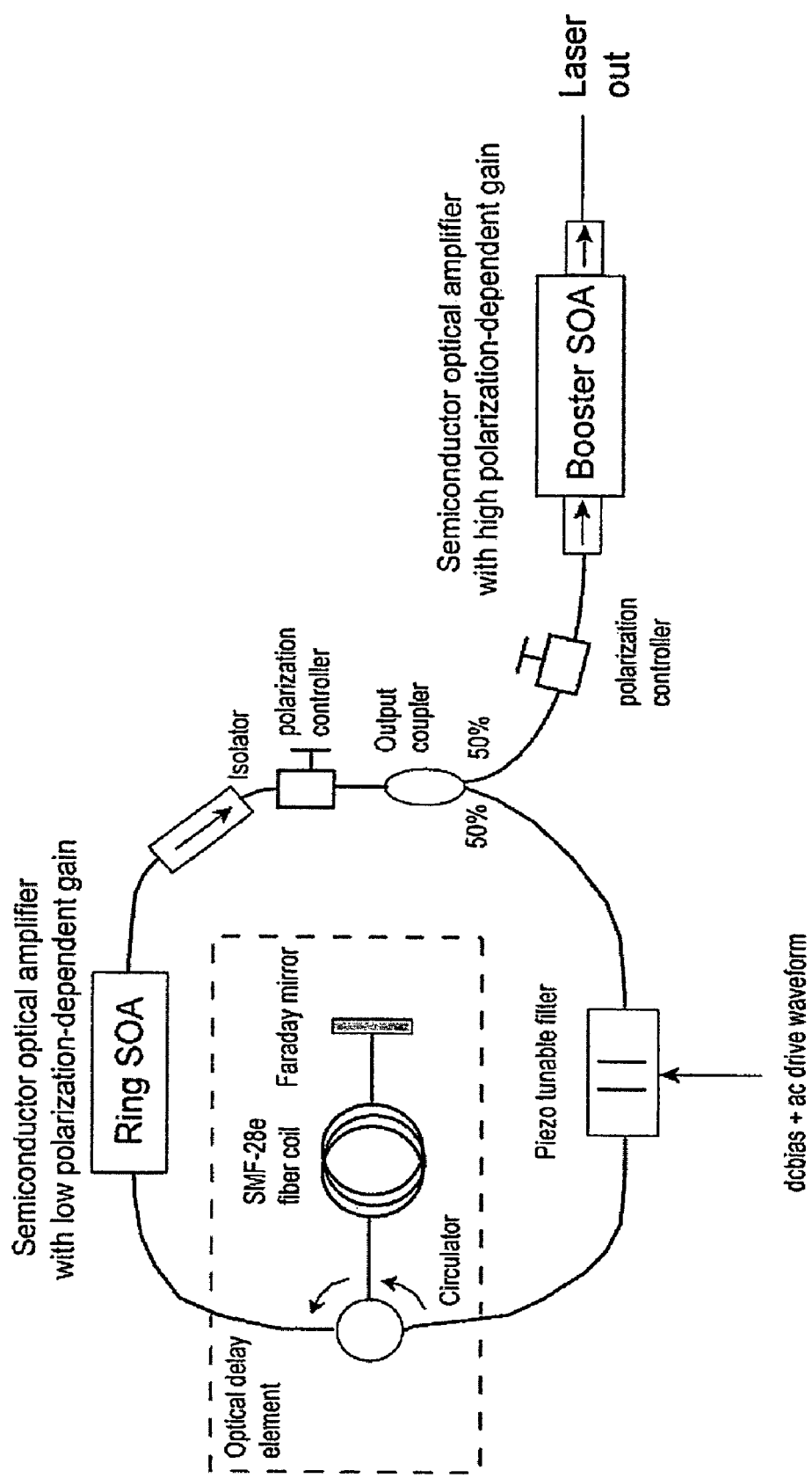
FIG. 2 shows a preferred embodiment of a FDML laser, configured to produce an output with high polarization stability according to an illustrative embodiment of the invention.
Figure 3:
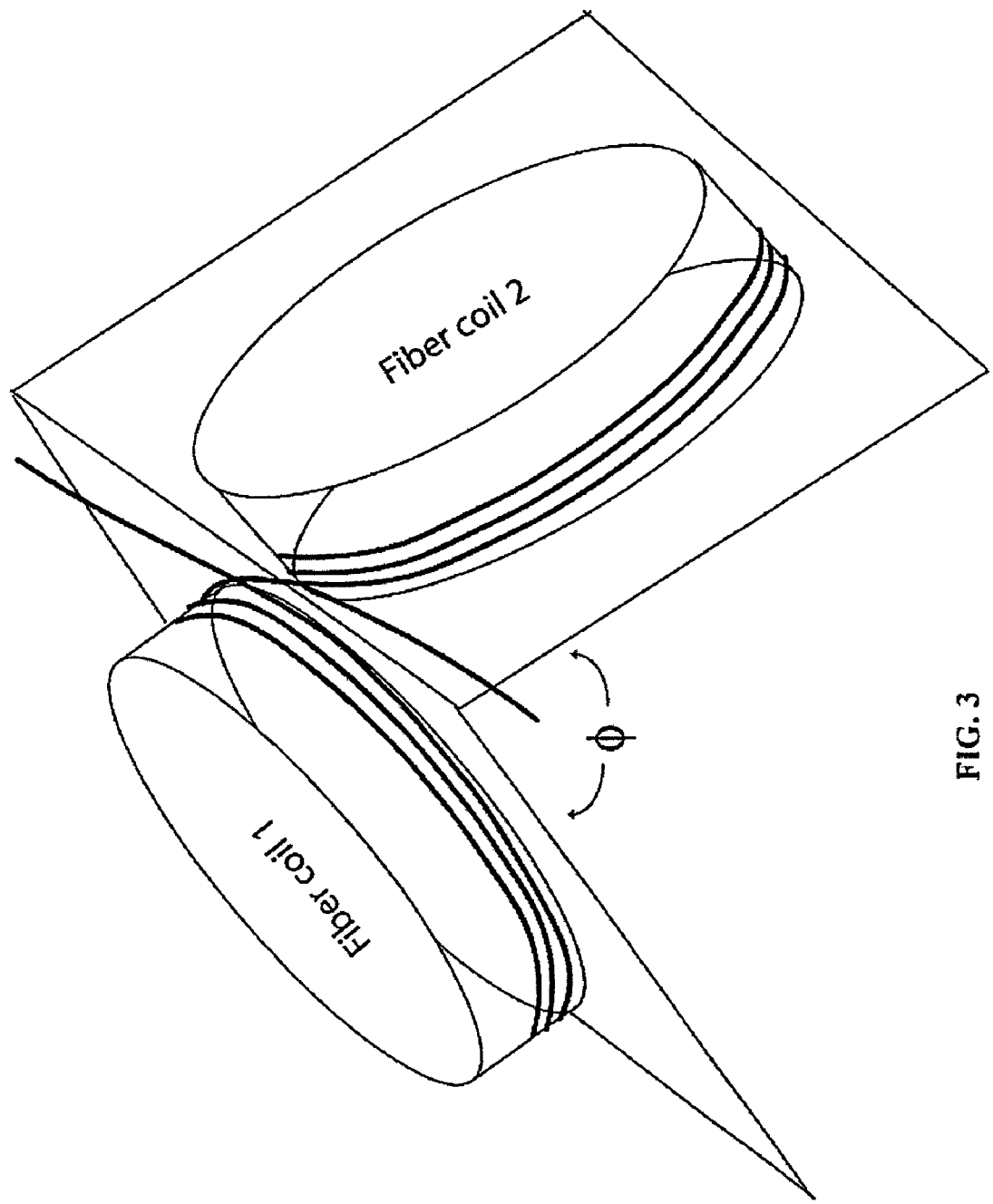
FIG. 3 shows an alternative design for the optical delay element in FIG. 2 that includes a pair of optical fiber coils oriented at an angle α~90 degrees for reducing polarization mode dispersion according to an illustrative embodiment of the invention.

General aspects of the invention and various embodiments illustrating systems and methods that address the problems recited above are described in more detail with respect to the accompanying figures. FIG. 1 illustrates a general implementation of a FDML based system $S_1$ suitable for use with an OCT probe. In turn, FIG. 2 provides specific details relating to the use of gain elements, such as, but not limited to semiconductor optical amplifiers to counteract unwanted polarization effects. Further, the system of FIG. 3 shows an alternative design for the optical delay element in FIG. 2 that includes a pair of optical fiber coils oriented at an angle $\alpha \sim 90$ degrees for reducing polarization mode dispersion according to an illustrative embodiment of the invention.

Returning to FIG. 1, a swept-source OCT (SS-OCT) system $S_1$ having various specific components is depicted. The main components of the system on which an embodiment of the invention is based are shown in FIG. 1. Specifically, FIG. 1 includes a tunable (wavelength-swept) laser L that includes an optical delay element 1; an optical frequency tuning element 2a; and a first gain element 2b The optical frequency tuning element 2a has one or more control inputs from a frequency-agile direct digital-synthesized waveform generator 3; and a digital-to-analog converter 4. This system $S_1$ is configured to achieve FDML and provide the benefits discussed above. Light, from the laser L, travels to a main interferometer which is in optical communication with an OCT probe. Light received from the OCT probe is transmitted back to the main interferometer and captured by a photoreceiver and ultimately converted to scan data.

As shown in FIG. 1, a microcontroller 5 for laser stabilization that receives a wavelength synchronization ($\lambda$ sync) input from a fiber Bragg grating filter 6 is also part of the system $S_1$. A sample clock generator 7 provides the sample clock directly to the main analog-to-digital converter (ADC). The system also includes a clock fringe control input from the sample clock generator 7 that is in electrical communication with the microcontroller 5. In general, all of the elements shown in FIG. 1 are in electrical or optical communication along the paths shown, as appropriate for a given embodiment.

As shown in the figure, light from an FDML laser L is split into a reference and sample path by the main interferometer. The electronic interference signal is detected by a balanced photoreceiver. In turn, the photoreceiver's output signal is processed at high speed by the main ADC. A small fraction of the light from the laser L enters the sample clock generator 7, which produces 1) a low-jitter sample clock for the main ADC and a 2) clock fringe signal that serves as the control variable for stabilization of the ac drive waveform of the frequency tuning element 2a.

Examples of frequency tuning elements include piezo-actuated Fabry-Perot filters and galvanometer-actuated grating filters. Another small fraction of the light from the laser L passes through a narrowband fiber Bragg grating filter into a third photoreceiver that generates a wavelength sync pulse. This sync pulse serves as the reference time marker for controlling the dc bias voltage of the frequency tuning element. The microcontroller performs the data acquisition and digital processing tasks associated with feedback control of the frequency of ac drive waveform and dc bias voltage. The ac drive frequency is controlled via a digital control word (typically 4 bytes or more) generated by the microcontroller to the direct digit synthesis (DDS) waveform synthesizer (e.g., Analog Devices AD9952).

Typically, the DDS synthesizer 3 is configured to generate a sinusoid in the 20-100 KHz range, whose frequency can be altered rapidly with a resolution better than 0.05 Hz. To produce a waveform with extremely low jitter, a high-frequency (typically >100 MHz), high stability (<10 ppm) oscillator, such as a crystal oscillator, can be used as the baseline clock for the DDS synthesizer 3. An additional digital control word generated by the embedded microcontroller and transmitted to a digital-to-analog converter (4), controls the dc bias of the frequency tuning element.

In contrast to the general overall system of FIG. 1, FIG. 2 shows a preferred embodiment of an FDML laser, configured to provide an output with high polarization stability. The embodiment of FIG. 2 can be used in the system of FIG. 1. The FDML laser of FIG. 2 addresses the problematic polarization effects introduced by mechanical and thermal stresses discussed above. Although the general layout is similar to that described by Huber et al (US Patent Application No. 2006/0187537), the first and second gain elements are chosen to satisfy specific requirements. In particular, the semiconductor optical amplifier (SOA) in the optical fiber ring (cavity), the first gain element, is chosen to provide low polarization-dependent gain (PDG). In turn, the booster semiconductor optical amplifier, an exemplary second gain element, is chosen to provide high polarization-dependent gain. The use of the terms "low" and "high" with respect to polarization-dependent gain (PDG) elements indicate the relative level of polarization-gain dependence such the polarization dependence of the high PDG element is greater than the polarization dependence of the low PDG element.

In one embodiment, a gain element, such as an amplifier, with a PDG less than about 3 dB can be considered a low PDG gain element. Conversely, in one embodiment, a gain element, such as an amplifier, with a PDG greater than or equal to about 3 dB can be considered a high PDG gain element. Further, in this context, a 3 dB PDG means that the two orthogonal polarization states are amplified to within 3 dB of each other.

In a conventional arrangement in which only a single SOA (either a high-PDG or low-PDG version) is used inside the ring or the SOAs with similar PDGs are used for both the ring and booster, large variations in the light's polarization state at the laser's output occur as the laser sweeps across a wide band of wavelengths. The wavelength dependence of the polarization-mode dispersion (PMD) within the optical delay element and the other optical elements inside the ring are the likely source of these effects. It is worth noting that the low PDG SOA does not eliminate the intra-sweep variations in the polarization state at the output of the laser, which can degrade the performance of the SS-OCT system.

The configuration described in FIG. 2 overcomes variations in both the amplitude and polarization, because the booster SOA (second gain element) provides sufficient amplification in a single polarization axis to reach gain saturation at all wavelengths, in spite of the polarization variations at the output of the low-PDG ring SOA (first gain element).

Turning now to FIG. 3, an alternative design for the optical delay element of FIG. 2 is shown. Specifically, in FIG. 3 the delay element shown includes a pair of optical fiber coils oriented at an angle $\phi \sim 90$ degrees for reducing polarization mode dispersion. The split-coil arrangement of the fiber optic delay element shown in FIG. 3 is designed to further reduce the effects of PMD inside the optical fiber ring that is used to match optical travel and electronic switching times in a FDML system. By orienting the coils at an angle $\phi$ that is substantially equal to 90 degrees, the group-delay difference between the orthogonal polarization modes in the first coil is compensated by an opposing difference in the second coil. This compensating effect results from the orthogonal orientations of the birefringence axes of the two coils. Thus, the embodiment shown in FIG. 3 further reduces unwanted polarization effects in the larger optical ring.

In general, aspects of the invention relate to the selection and matching of components for use in an FDML OCT system. The selection of the sample clock generator is another aspect of the invention. As shown in FIG. 1, the sample clock generator 7 is in communication with different controls and the FDML laser. The function of the sample clock is twofold. First, it is used to generate a sample clock for the main analog-to-digital converter and, second, to generate a clock fringe control signal for use by the microcontroller 5.

As shown in FIG. 1, the microcontroller 5 uses the clock fringe control signal to determine a substantially optimum drive frequency for controlling the frequency tuning element connected to or integrated within the FDML laser. The sample clock generator derives low-jitter clock pulses from the sinusoidal interference signals generated by the sample clock interferometer. Although the time intervals of the clock pulses vary as the wavelength of the laser sweeps, equal spacing of the intervals between the clock edges in the optical frequency domain is maintained. These characteristics allow direct clocking of certain types of high-speed analog-to-digital converters, such as flash A/D converters or pipelined A/D converters that accept a variable frequency clock (e.g., AD9340), without the need for complex resampling hardware. Thus, given the significance of synchronizing optical trains in a FDML system the selection of the clock generator and various enhancements relating thereto improve the overall quality of the scan data obtained from an OCT probe. Additional details relating to sample clock generator embodiments are described and/or shown in more detail below with respect to FIGS. 4-10.

Figure 4:
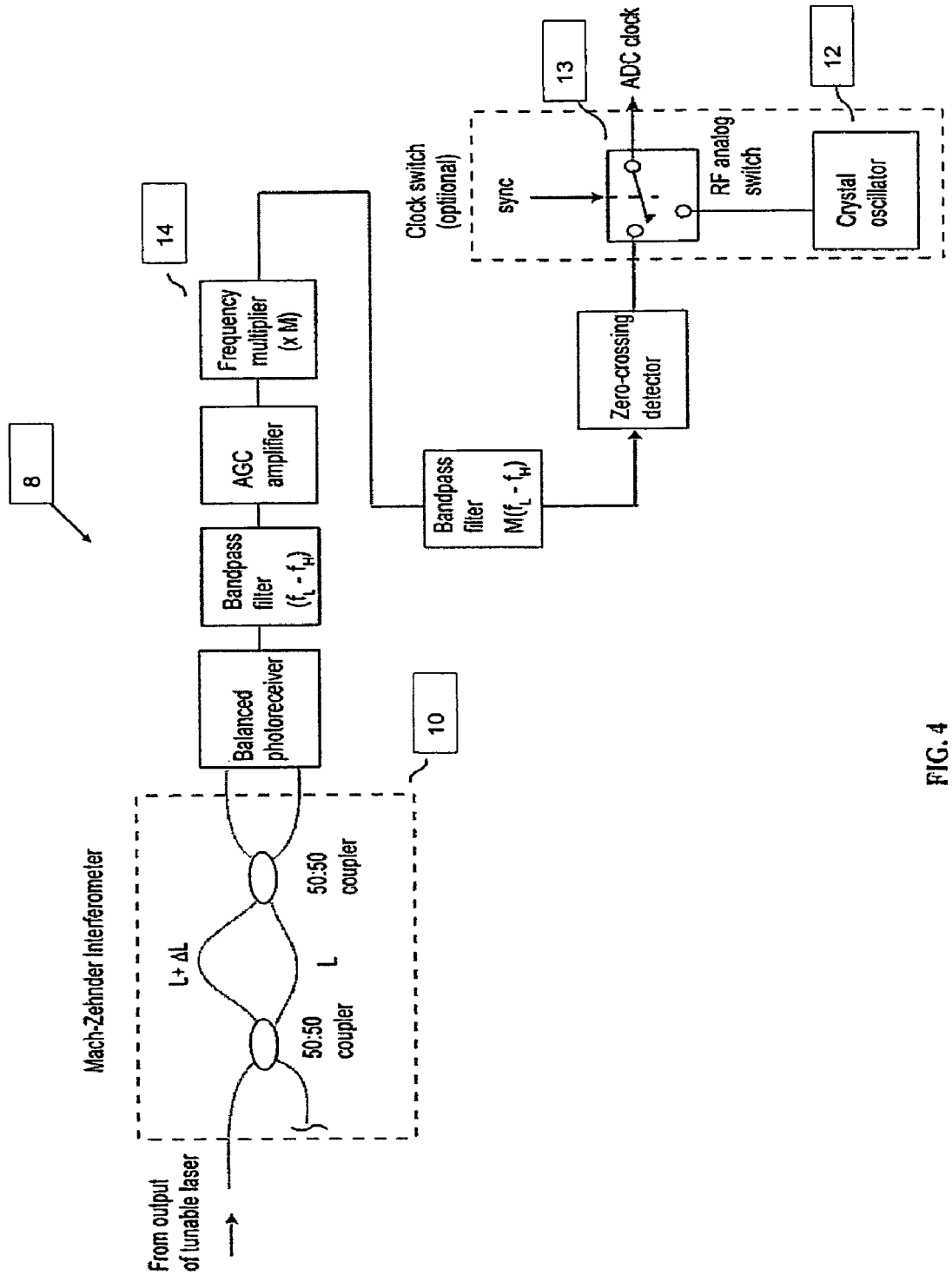
FIG. 4 shows a general embodiment of a sample clock generator according to an illustrative embodiment of the invention.
Figure 5:
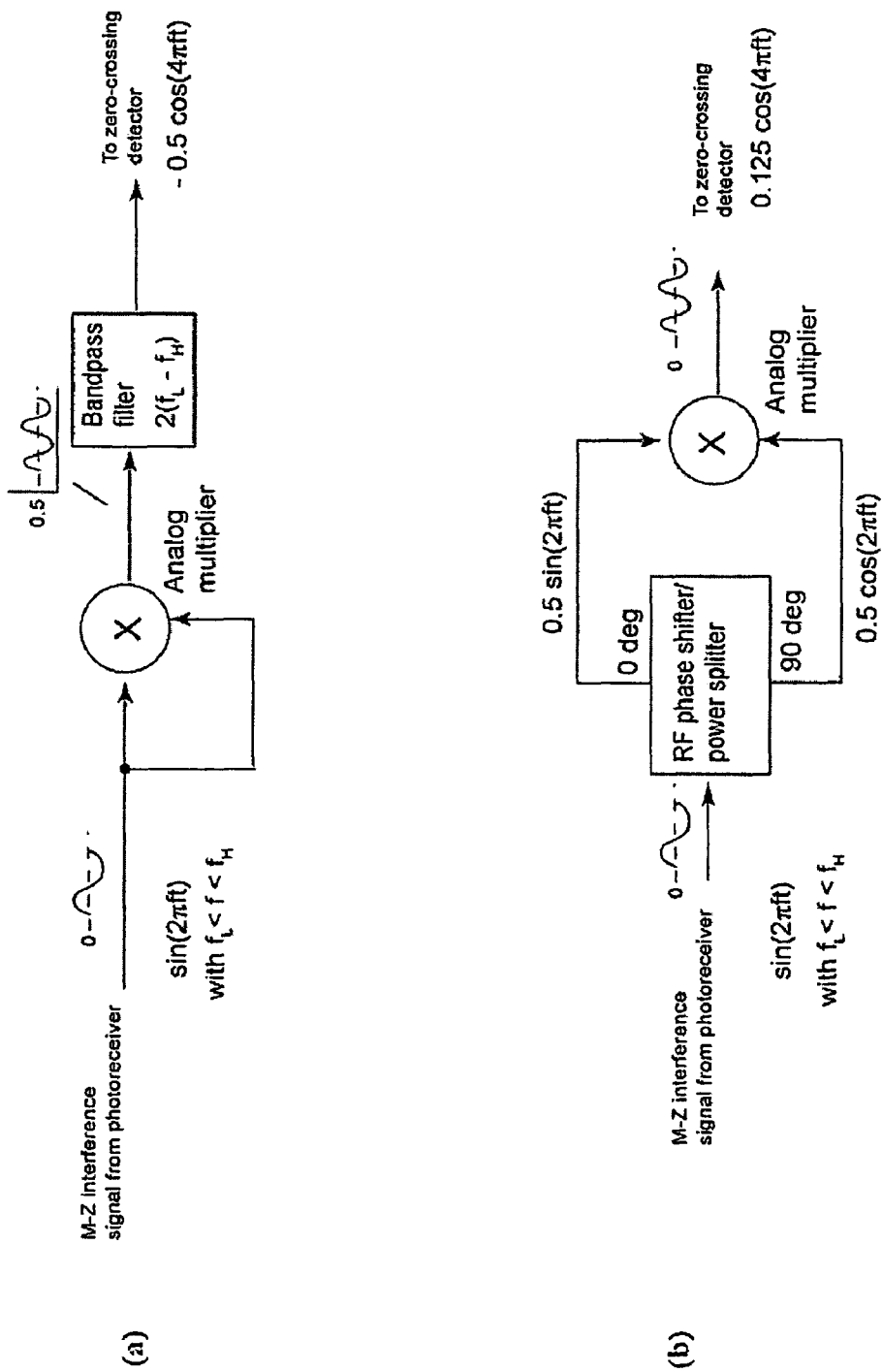
FIG. 5 shows two specific embodiments, 5(a) and 5(b), of the frequency multiplier in FIG. 4 according to illustrative embodiments of the invention.

FIG. 4 shows a general embodiment of a sample clock generator 8 that derives a stable analog-to-digital converter (ADC) clock from the balanced outputs of a Mach-Zehnder interferometer 10. The frequency multiplier (4) (M=2, 3, . . . ) permits ADC clocking at rates higher than the fundamental frequency of the Mach-Zehnder interference signals. In one embodiment, the generator includes an optional set of components such as a crystal oscillator 12 and RF clock switch 13 that permit the use of analog-to-digital converters that provide non-interrupted clocking.

As depicted, FIG. 4 illustrates the basic configuration of the sample clock generator 8. A photoreceiver converts the optical interference signals from the sample clock interferometer shown in this embodiment as the Mach-Zehnder interferometer 10 with an optical path imbalance equal to ΔL, into a chirped sinusoidal waveform. The waveform is filtered to pass the band of frequencies generated by sweeping the FDML laser between its wavelength limits. To equalize the amplitude of the interference signals generated during the sweep and to reduce phase errors after zero-crossing detection, the filtered waveform passes thorough an amplifier with automatic gain control (AGC).

An optional frequency multiplier 14 multiplies the frequency of the band-passed waveform, typically by a factor of 2 to 4. The frequency multiplier 14 (M=2, 3, . . . ) permits ADC clocking at rates higher than the fundamental frequency of the Mach-Zehnder interference signals. Because it allows swept-source lasers to generate synchronous ADC clocking rates above the Nyquist frequency when the path length imbalance is set equal to the coherence length of the laser, frequency multiplication enhances the operation of clock generators designed for use with high-resolution SS-OCT systems with long scan ranges. After frequency multiplication, the waveform is filtered again to eliminate undesired harmonics and the residual signal components at the fundamental frequency.

In turn, in the embodiment of FIG. 4, a zero-crossing detector converts the waveform into a pulse train with variable spacing in the time domain, but equal spacing in the optical frequency domain. An optional clock switch, composed of a crystal oscillator and RF switch, interposes a fixed frequency pulse train between variable-frequency pulse trains generated during the periodic sweep interval. The clock switch permits the use of analog-to-digital converters that require non-interrupted clocking.

Two alternative embodiments of the frequency multiplier of FIG. 4 are depicted in FIGS. 5a and 5b. Specifically, the two frequency multiplier embodiments shown are designed for doubling (M=2) the frequency of sinusoidal interference signals with frequencies that sweep over the range $f_L$ to $f_H$ during the acquisition period according to illustrative embodiments of the invention. In FIG. 5a, an analog multiplier is configured as a squarer, with both its inputs derived from the output of the balanced photoreceiver in FIG. 4.

In FIG. 5a, the frequency multiplied is an analog RF multiplier (e.g., Analog Devices AD834 or AD835) configured as a frequency doubler. This configuration performs a squaring function on a sinusoidal input to produce a sinusoid at twice the frequency. A bandpass filter eliminates the offset introduced by the squaring process. Another version of the embodiment of FIG. 5a is shown in FIG. 5b. In FIG. 5b, the frequency doubler splits the input sinusoidal waveform into two waveforms with a relative phase difference of 90 degrees.

In FIG. 5b, a phase-shifting power splitter is used to generate a pair of sinusoidal signals with 90-degree phase difference, approximately independent of frequency. The two outputs are fed into an analog multiplier to produce a sinusoid at twice the frequency. The phase-shifted sinusoids are multiplied together to produce a sinusoid at twice the frequency.

Unlike the FIG. 5a embodiment, the embodiment of FIG. 5b does not require a bandpass filter, because no offset is introduced by the multiplication process.

Figure 6:
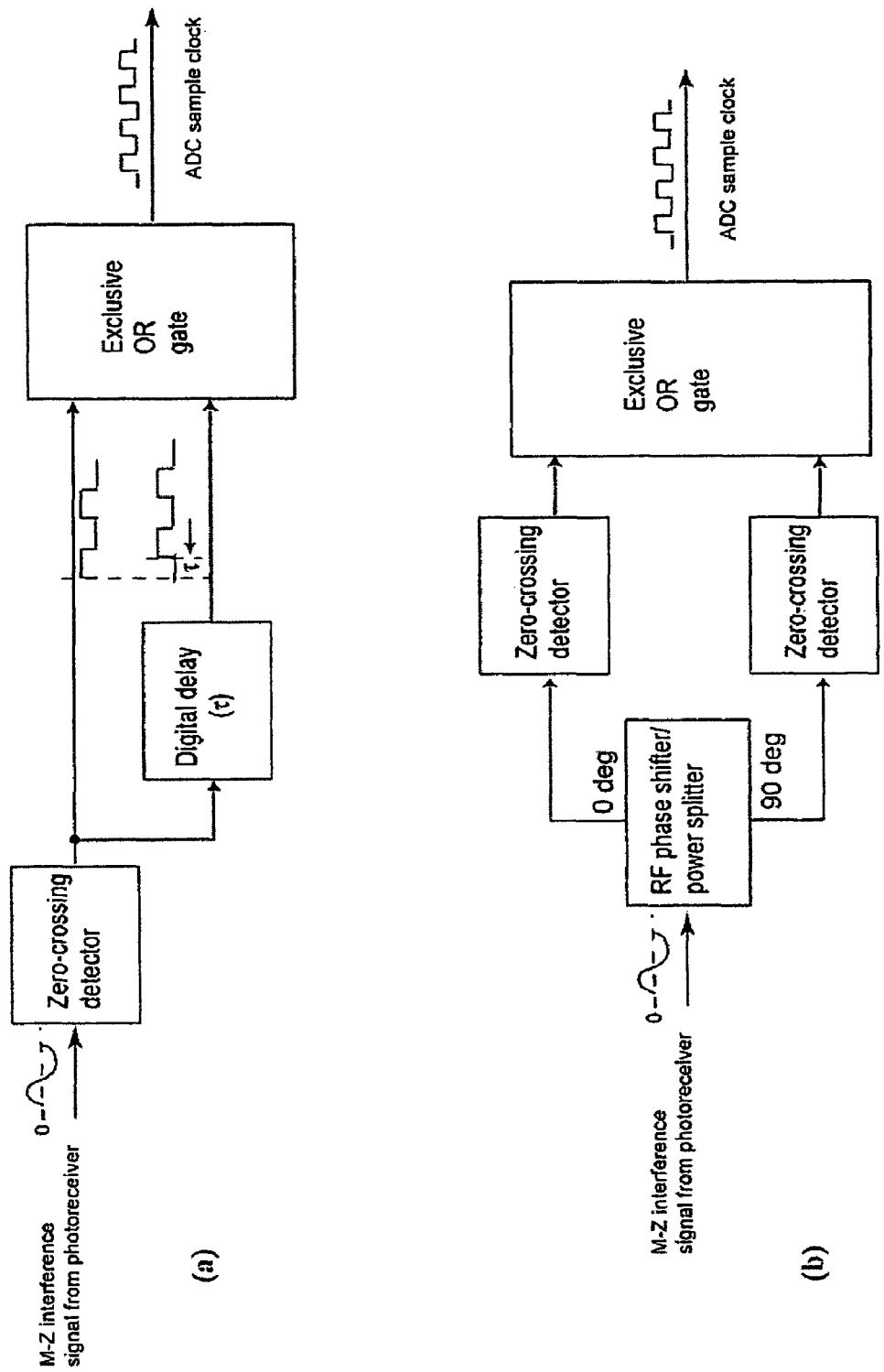
FIG. 6 shows two additional embodiments, 6(a) and 6(b), of frequency multipliers according to illustrative embodiments of the invention.

FIG. 6 shows two additional frequency multiplier embodiments that are designed for clock frequency doubling according to illustrative embodiments of the invention. In the embodiment in FIG. 6a, a zero-crossing detector first converts the sinusoidal output of the sample clock interferometer into a square wave. A delayed version of the square-wave is then exclusive-ORed with itself to produce an ADC clock with twice the frequency of the input sinusoidal waveform. The delayed pulse train is generated by a digital delay line, set for a delay τ equal to ¼ of the shortest interpulse interval.

In the embodiment in FIG. 6b, a pair of sinusoidal signals with a 90-degree phase difference is generated with a phase-shifting power splitter. Specifically, the input sinusoidal waveform is split by a power splitter into two waveforms with a relative phase difference of 90 degrees. These signals are then converted into square waves that are exclusive-ORed to produce the frequency-doubled ADC clock. This embodiment has the advantage that the sample clock maintains a constant 50% duty cycle over a wide frequency range. To enhance most pipelined analog-to-digital converters performance, they are driven with a duty cycle close to 50%.

Figure 7:
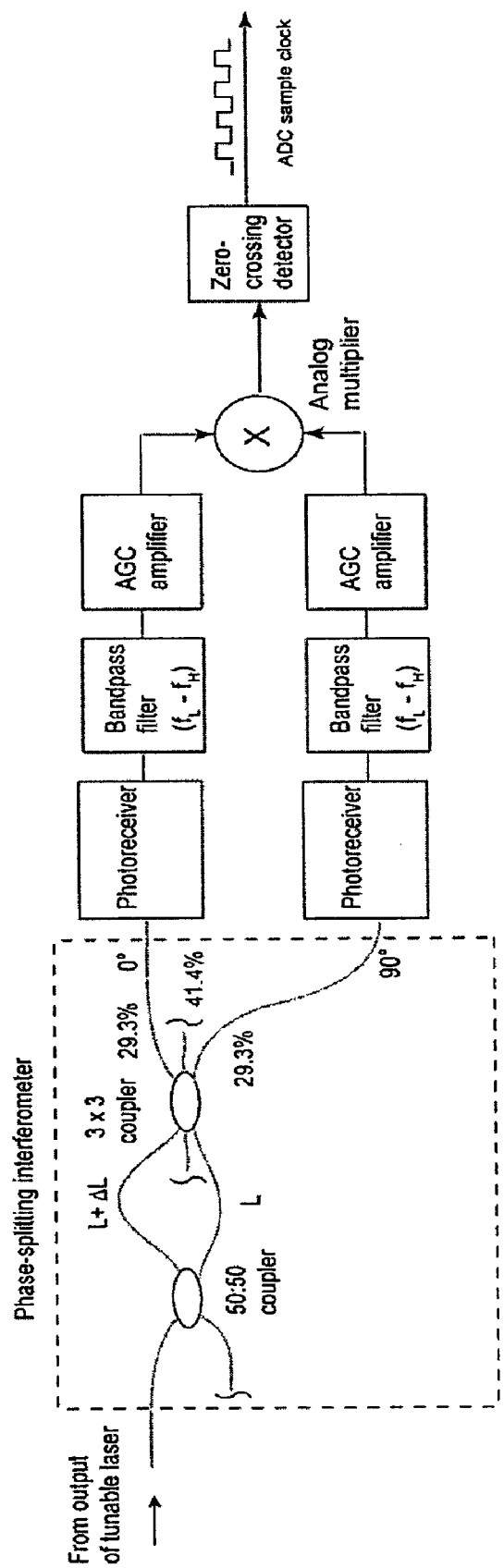
FIG. 7 is another embodiment of the sample clock generator in which the Mach-Zehnder sample clock interferometer is replaced by a 3×3 phase-splitting interferometer according to an illustrative embodiment of the invention.
Figure 8:
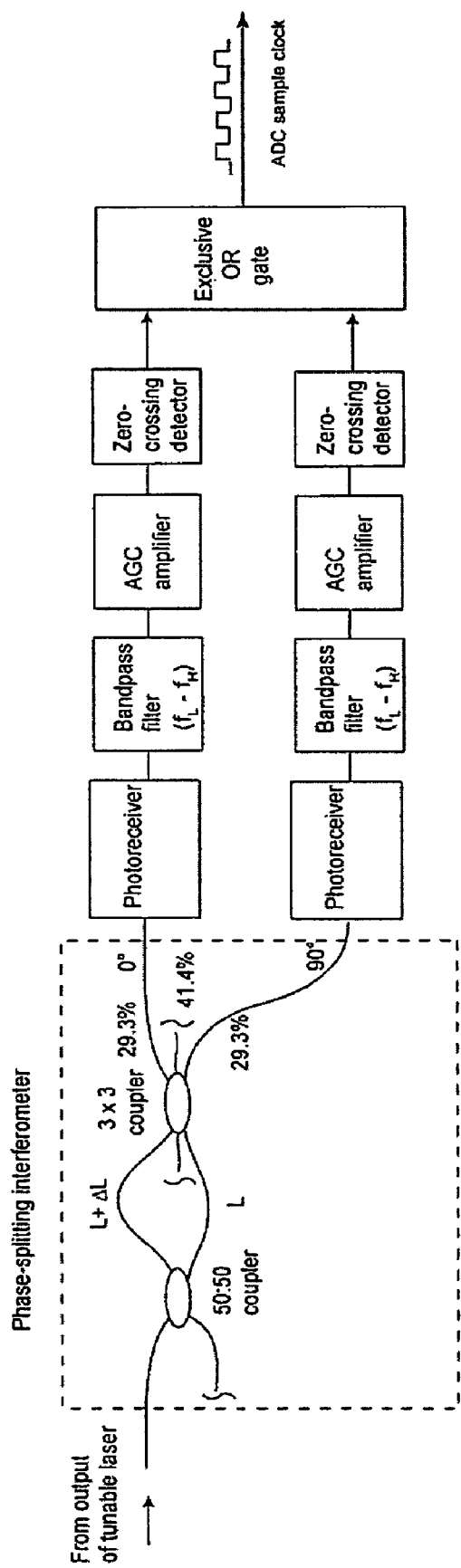
FIG. 8 is a modified version of the sample clock generator shown in FIG. 7, in which the two quadrature outputs are first passed though zero-crossing detectors and then exclusive-ORed to generated the frequency-doubled ADC clock according to an illustrative embodiment of the invention.
Figure 9:
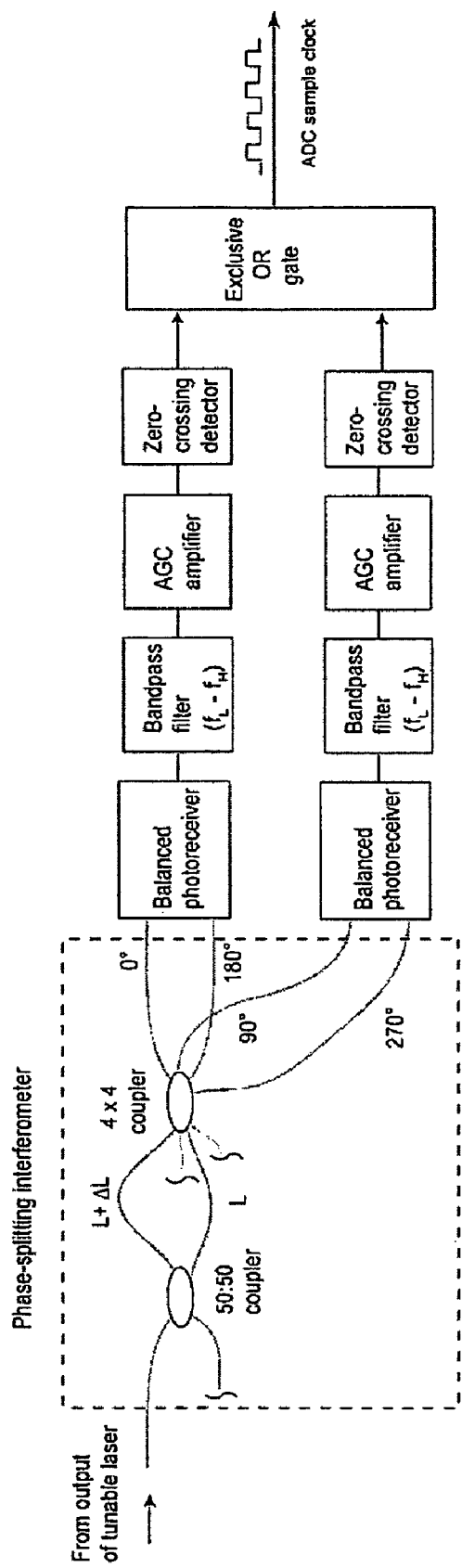
FIG. 9 is yet another embodiment of the sample clock generator according to an illustrative embodiment of the invention.

The delay required for frequency multiplication of the interference signals can be realized in the optical domain as well as the electrical domain, as illustrated by the embodiments of the sample clock generators shown in FIGS. 7-9. These embodiments take advantage of the phase relationships among optical signals that combine within interferometers based on N×N fiber couplers.

For example, the phase-splitting interferometer in FIG. 7 is fabricated by replacing the output 2×2 coupler of a conventional Mach-Zehnder interferometer (having an optical path imbalance equal to ΔL) with a 3×3 coupler. When the 3×3 coupler has a specific splitting ratio (~about 29.3%:~about 41.4%:~about 29.3%), the interference signals formed at two of its outputs have a relative phase difference of 90 degrees. In the embodiment of FIG. 7, the power-splitting ratio about 29.3%:about 41.4%:about 29.3% is chosen to provide two equal-amplitude outputs with quadrature phase. These two outputs are multiplied and passed through a zero-crossing detector. Thus, the electrical signals can be processed separately and mixed in an analog multiplier to form a frequency-doubled sinusoidal waveform. Alternatively, as shown in FIG. 8, the phase-shifted optical signals can be processed by using the digital XOR technique (discussed above) to produce a frequency-doubled ADC sample clock.

In systems in which balanced photodetection is required to reduce degradation of the clock signal caused by laser intensity noise, the embodiment in FIG. 9 may be preferred. As shown, two pairs of phase-shifted optical signals with opposite polarities are formed by replacing the output 2×2 coupler of a conventional Mach-Zehnder interferometer with a 4×4 coupler that splits the optical power equally among its four outputs. This embodiment is based on a 4×4 phase-splitting interferometer that provides a pair of balanced outputs with quadrature phase relationship. As in the FIG. 8 embodiment, the resultant optical signals are processed digitally using XOR techniques to produce a frequency-doubled ADC sample clock.

Figure 10:
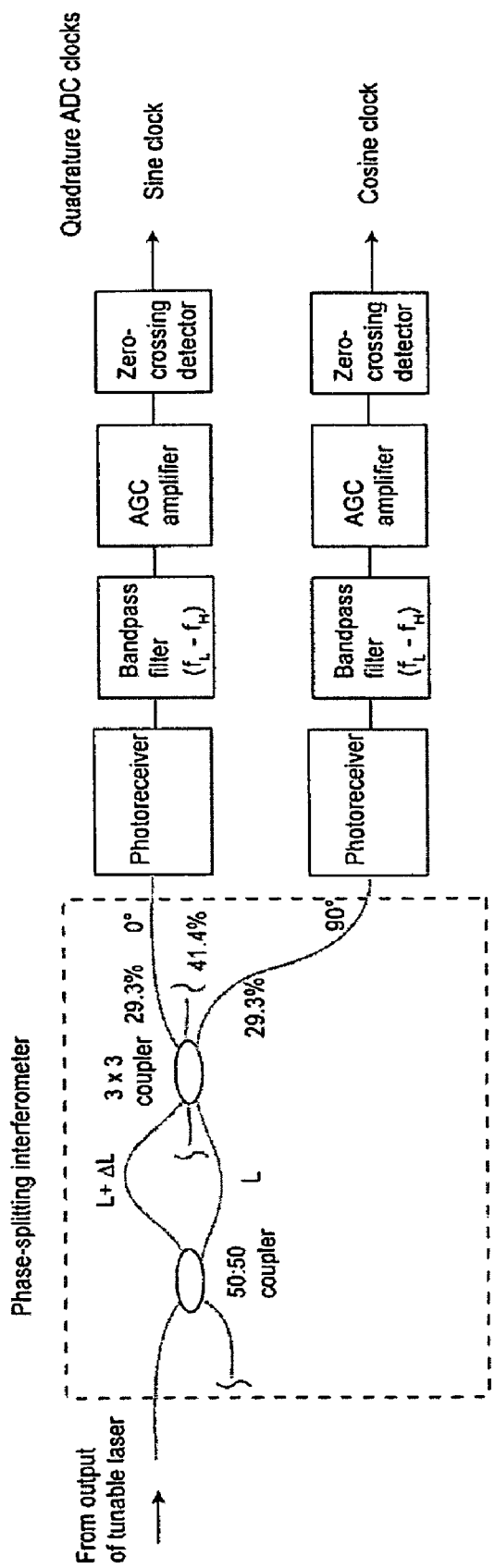
FIG. 10 shows a configuration in which the quadrature sample clocks are employed as separate clocks for quadrature detection of OCT signals from the main interferometer according to an illustrative embodiment of the invention.

FIG. 10 illustrates yet another embodiment of the sample clock generator. Unlike the embodiments in FIGS. 4-9, this embodiment produces two separate ADC sample clocks with a quadrature phase relationship. These Sine and Cosine clocks can be used to acquire OCT interference signals from the main interferometer on parallel ADC channels at the fundamental sampling frequency set by the optical path imbalance (ΔL) of the sample clock interferometer.

Figure 11:
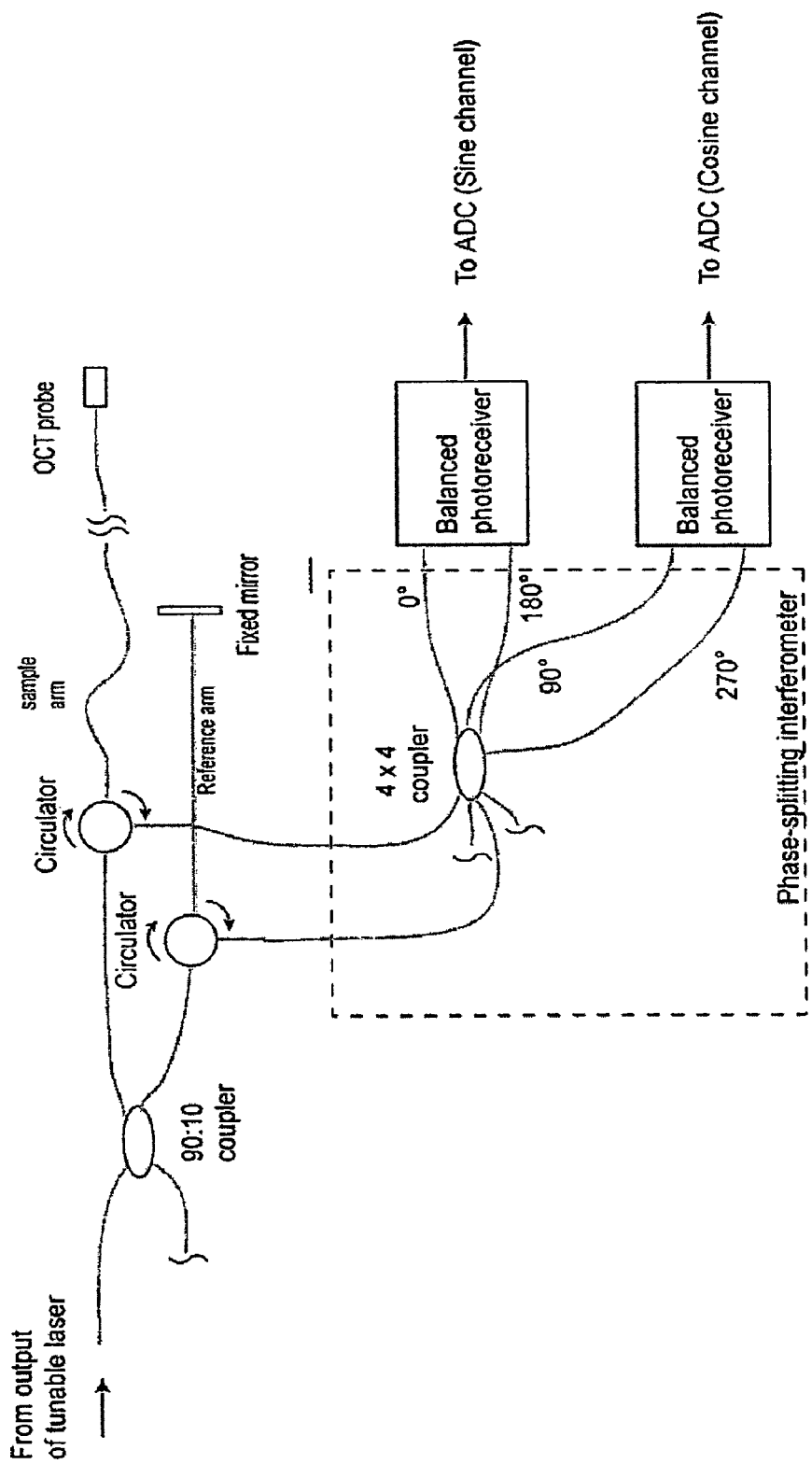
FIG. 11 depicts the application of a 4×4 optical coupler for dual-channel acquisition of balanced quadrature OCT signals from the main interferometer according to an illustrative embodiment of the invention.

Complex Fourier transformation of OCT signals permits reconstruction of the depth profile of the sample, while suppressing image artifacts that arise from complex conjugate ambiguity. SS-OCT systems that reconstruct depth profile via Fourier transformation of real-valued interference signals suffer from artifacts generated by the superposition of reflectors offset by equal distances on either side of the reference reflector. As shown in FIG. 11, an analogous optical phase-splitting method can be used to collect quadrature (complex) signals from the main interferometer by using a pair of ADC converters clocked simultaneously with the same ADC clock.

In SS-OCT systems based on an FDML laser, precise control of both the ac drive waveform, which sets the laser repetition rate, and dc bias of frequency-tuning element, which sets the center wavelength of the sweep, is required to attain high signal-to-noise and wide dynamic range. In one embodiment, the optimum ac drive frequency is defined as the frequency at which the instantaneous linewidth of the laser is a minimum, which occurs when the round-trip time in the cavity and the period of the waveform match. At this frequency, when measured at the time $t=\tau$ at which the laser scans through the zero-dispersion wavelength of the optical delay element (typically 1310-1315 nm), the instantaneous RMS amplitude $\Phi(t)$ of the interference signal at the output of the sample clock interferometer's photoreceiver reaches a maximum. Therefore, the optimum drive frequency can be found by adjusting the drive frequency to maximize $\Phi(\tau)$.

Figure 12:
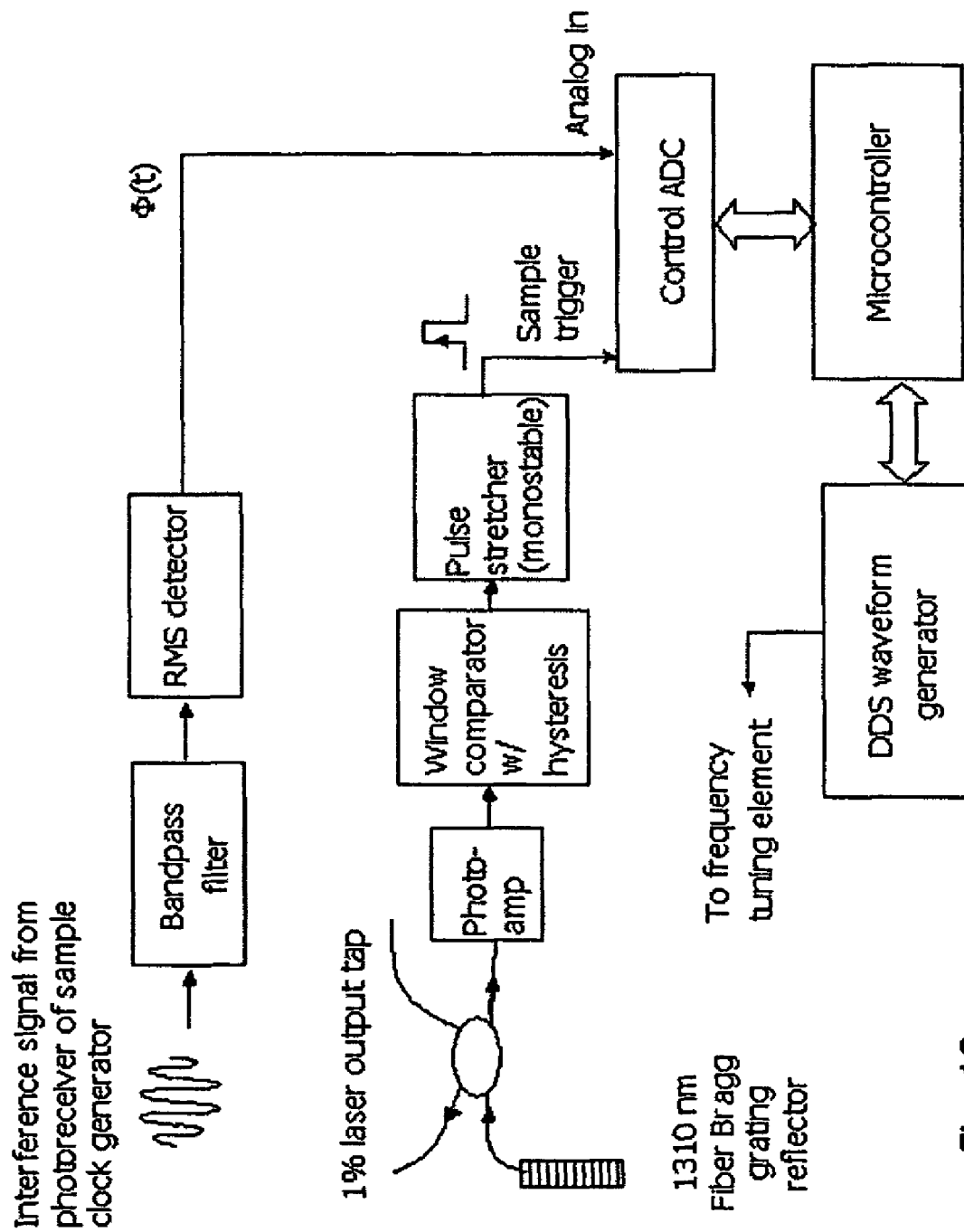
FIG. 12 illustrates a specific embodiment of a digital feedback loop for optimization and stabilization of the drive frequency of an FDML-based SS-OCT system according to an illustrative embodiment of the invention.

FIG. 12 shows one of the preferred embodiments of a digital feedback loop, which is based on a microcontroller that records $\Phi(t)$ with an analog-to-digital converter at the time indicated by transmission of the pulse through a fiber-Bragg filter with a narrow passband (typically<1 nm) at 1310 nm. The microcontroller adjusts the frequency of a low-jitter, frequency-agile DDS waveform generator until the recorded value of $\Phi(t)$ attains its maximum value. With respect to the embodiment of FIG. 12, the clock fringe control signal is obtained by detecting the instantaneous RMS amplitude of the bandpass-filtered interference signal from the sample clock generator's photoreceiver. The RMS amplitude is sampled by the control ADC at the time at which the frequency tuning element scans through the zero-dispersion wavelength (1310 nm) of the optical delay element in the FDML laser.

Figure 13:
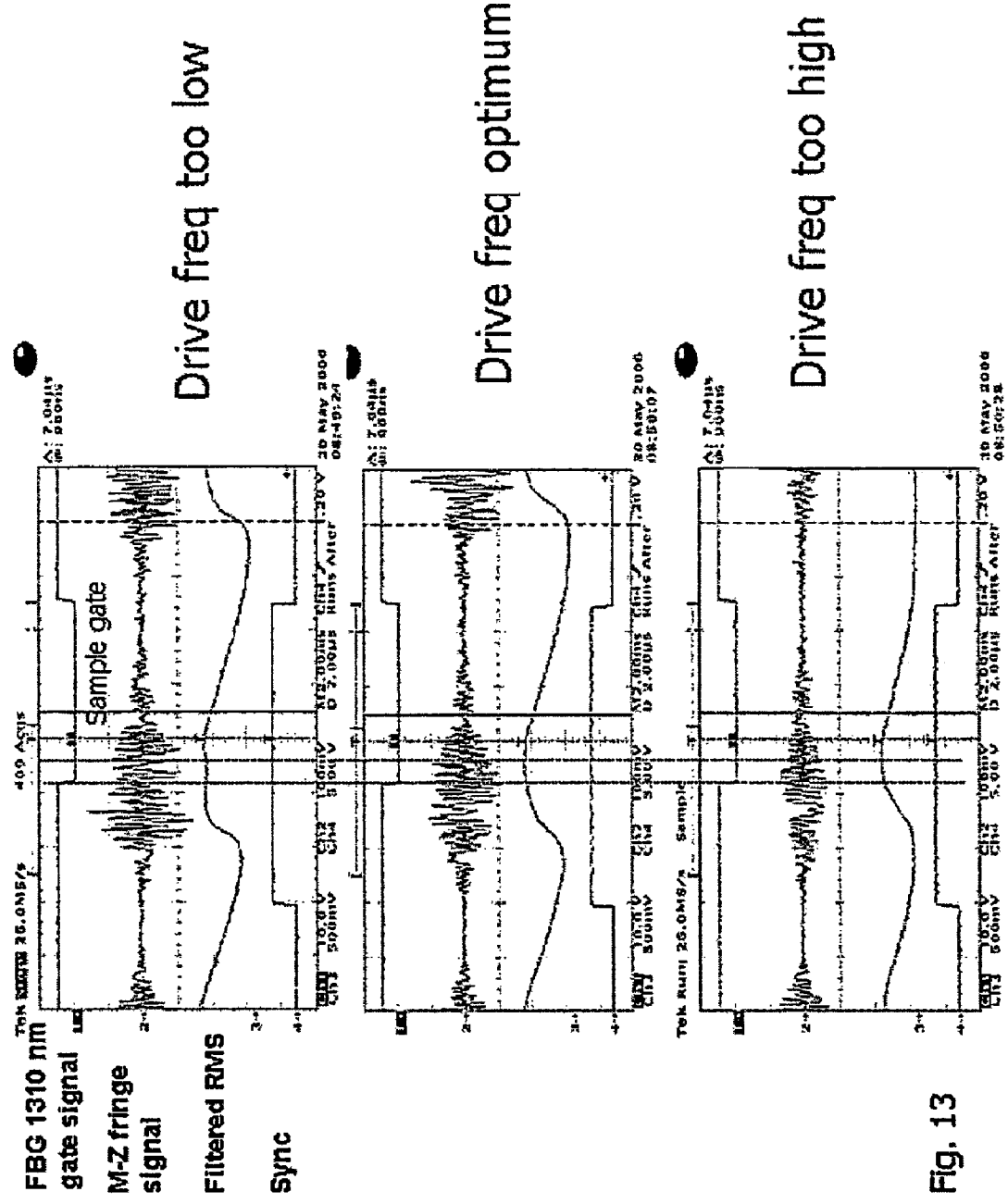
FIG. 13 shows the measured amplitudes and shapes of the clock fringe control signal (RMS fringe amplitude) for optimum and non-optimum (too low or too high) adjustment of the frequency of the waveform driving the frequency tuning element in the FDML laser according to one specific embodiment of the invention.

Turning now to FIG. 13, the figure illustrates how the instantaneous RMS amplitude of the sample clock interference signal varies at the optimum adjustment frequency and at frequencies above and below the optimum. The frequency of the waveform can be updated either continuously or at intermittent intervals determined by the maximum drift of the laser. In addition to its ac drive waveform, the dc bias of the frequency-tuning element is adjusted to achieve optimum performance of the FDML-based SS-OCT system.

Figure 14:
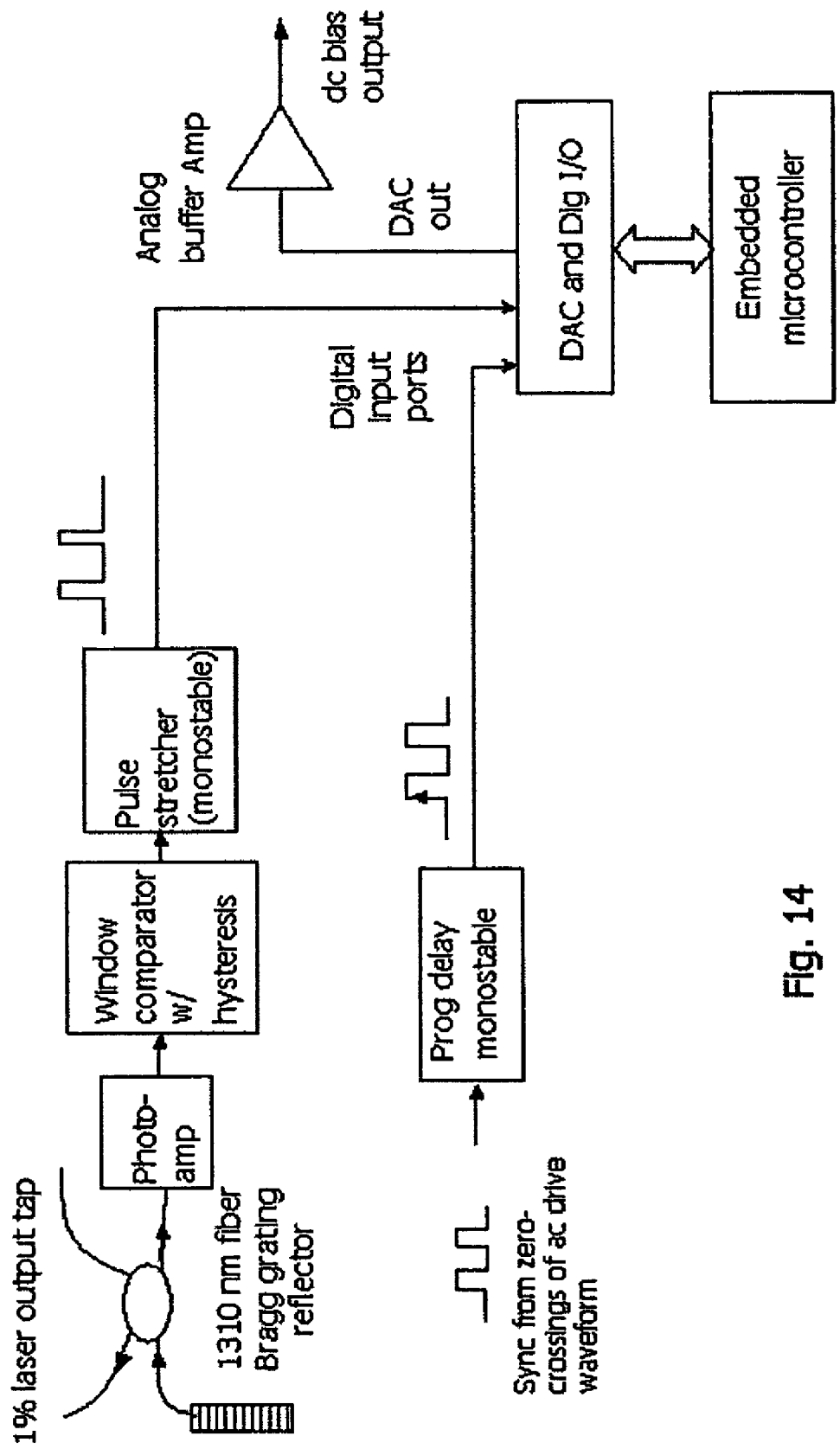
FIG. 14 illustrates a specific embodiment of a feedback control loop for optimization and stabilization of the dc bias voltage applied to the tuning element in the FDML laser according to an illustrative embodiment of the invention.

One embodiment of a digital control loop for optimizing the dc bias is shown in FIG. 14. That is, the loop adjusts the amplitude of the DC bias until the time at which the frequency tuning element scans through the zero-dispersion wavelength (1310 nm) coincides with a fixed delay after the ac drive waveform crosses zero. This loop adjusts the dc bias such that the wavelength scan of the laser starts at a fixed wavelength, regardless of environmental influences that alter the voltage sensitivity of the tuning element. The same fiber Bragg filter as that employed in the frequency optimization control loop (FIG. 13) is employed as a wavelength reference. By adjusting the dc bias via a digital-to-analog converter (DAC), the microcontroller maintains the time interval at a constant level between the zero-crossings of the ac drive waveform from the DDS generator and the edge of the pulse generated by a comparator at the output of a photoamplifier connected to fiber Bragg filter.

The relationship and commercial feasibility associated with waveform generation, filter design, and laser behavior is important to consider when implementing the systems disclosed herein. Although (1) sinusoidal waveforms are easy to generate with inexpensive DDS integrated circuits and (2) most high-speed tunable filters with highly resonant responses operate best with sinusoidal actuation, this beneficial application of sinusoids does not extend to all lasers. For example, lasers with linear, rather than sinusoidal wavelength sweeps, provide higher performance light sources for SS-OCT systems. With sinusoidal wavelength sweeping, the instantaneous sampling clock frequency varies over a wide frequency range in proportion to the slope of the sine wave over its period. Typically, precision high-speed analog-to-digital converters accept clock frequencies over a prescribed range (e.g., about 40-about 210 MHz). Consequently, the effective duty cycle over which interferometric measurements can be acquired is, typically, limited to about 33%. In addition, the Nyquist sampling frequency varies continuously and rapidly in proportion to the sampling clock frequency. The use of tracking filters and the linearization approaches described herein in various embodiments overcome this effective duty cycle limit.

Therefore, in one embodiment, to avoid aliasing, which results in objectionable foldover artifacts in OCT images, the cut-off frequency of the anti-aliasing filter applied to the interference signal before analog-to-digital conversion is configured to track ½ (or less) of the instantaneous sampling frequency. Suitable tracking filters can be assembled by using, for example, varactor-tuned LC circuits. However, proper synchronization of the tracking controller requires complex digital or analog control circuitry and to achieve the required sharpness, the filter is typically built from multiple stages with narrow component tolerances. In contrast, linearizing the wavelength sweep of the tunable filter over a large fraction of the wavelength sweep can provide an alternate solution in some embodiments.

Using the Mach-Zehnder clocking methods described herein, a high-duty-cycle linear wavelength sweep produces a large number of sample clock pulses with a narrower frequency distribution than a sinusoidal wavelength sweep. Thus, higher speed imaging can be achieved with less foldover artifacts at lower maximum data acquisition speeds. Unfortunately, linear actuation of commercially available Fabry-Perot tunable filters at high speeds is difficult to achieve using conventional triangular or ramp waveforms, because such broadband waveforms contain frequencies that excite strong resonant behavior of the actuators. Excitation of the filters with ramp or triangular drive waveforms produces near-sinusoidal oscillations at the mechanical resonance frequency rather than the desired linear scan.

Figure 15:
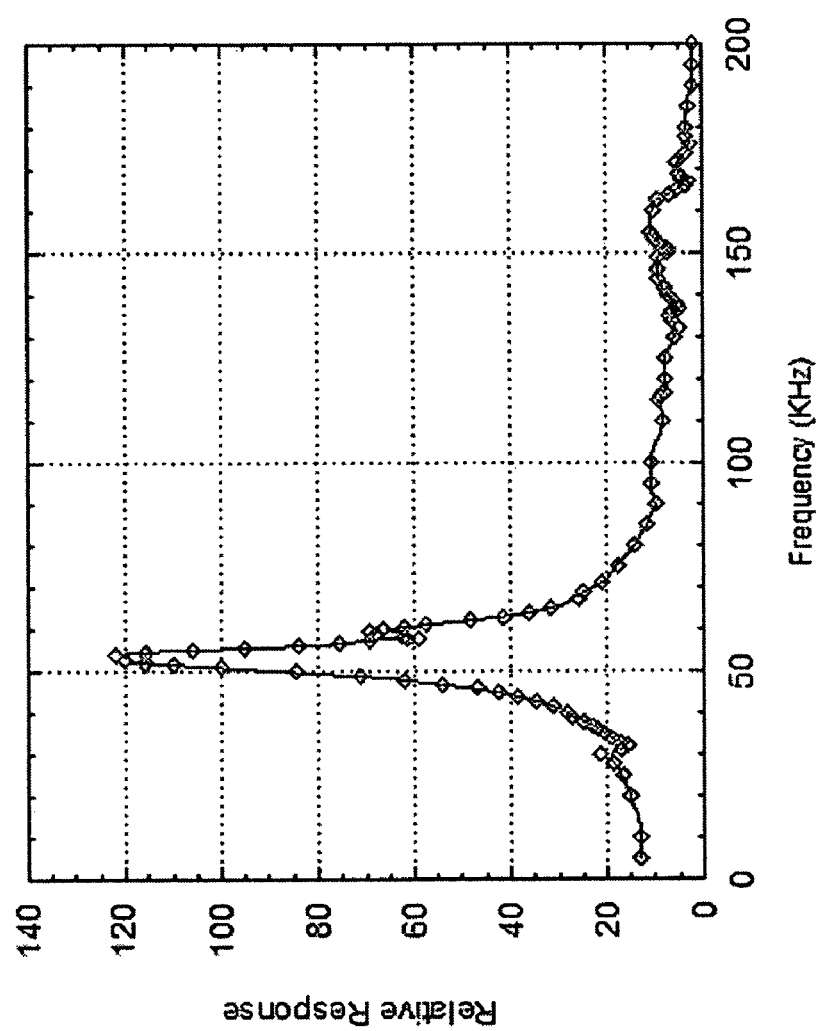
FIG. 15 shows the typical highly resonant frequency response of a piezo-actuated Fabry-Perot tunable filter according to an illustrative embodiment of the invention.

As illustrated by the measured frequency response in FIG. 15, piezo-actuated filters typically exhibit the mechanical resonance with a high quality factor (Q=4-8) at frequencies in the 40-75 KHz range. To achieve triangular or ramp excitation of these filters, the drive waveform is tailored to provide linear mechanical response over an extended period while compensating for the highly non-uniform amplitude and phase responses of a given filter.

Figure 16:
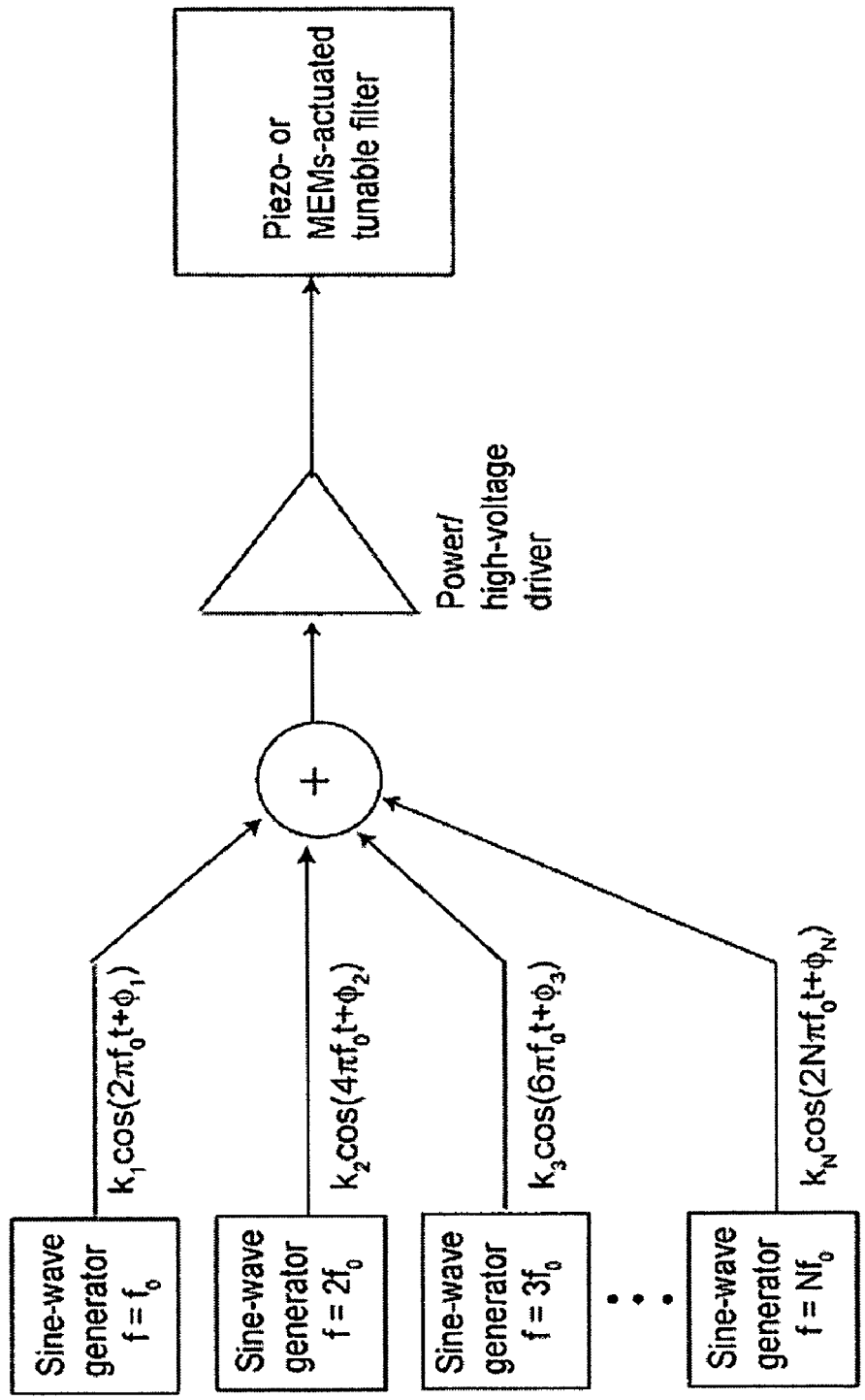
FIG. 16 illustrates the principle of Fourier synthesis on which an exemplary actuator linearization method is based according to an illustrative embodiment of the invention.
Figure 17:
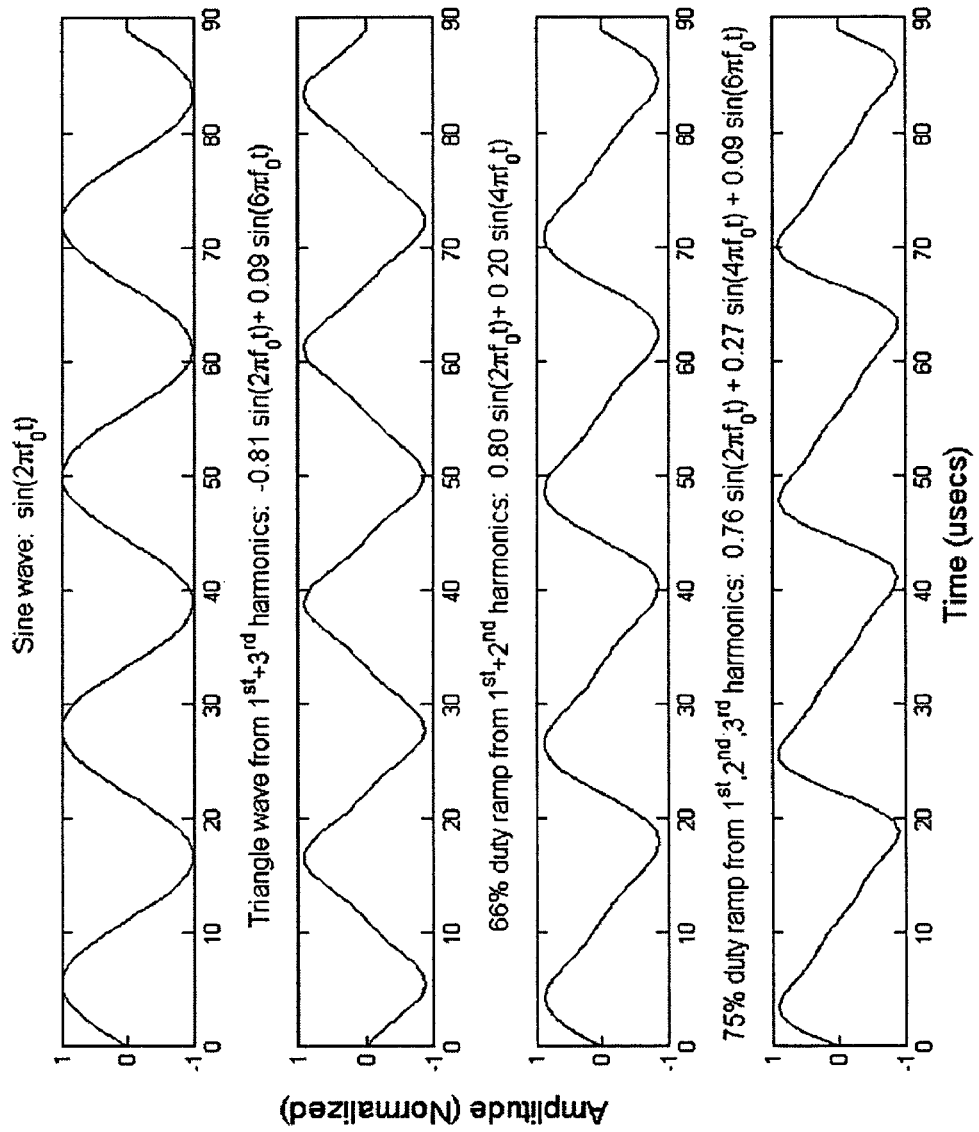
FIG. 17 shows an example of a configuration for synthesized harmonic linearization of a piezo-actuated Fabry-Perot tunable filter according to an illustrative embodiment of the invention.

Further, FIG. 16 illustrates a novel means of synthesizing a drive waveform based on the summation of harmonically related sinusoids according to the principal of Fourier synthesis. The period of near-linear amplitude decay of the drive waveform can be extended significantly by forming the weighted sum of only 2 or 3 harmonics of the fundamental sine wave. The example waveforms are shown for $f_0=45$ KHz. A first advantage of this method is that the fundamental and harmonic frequencies of the sine waves can be chosen to avoid the strong resonances in the mechanical response of the filter. In turn, a second advantage of this method, as illustrated in FIG. 17, is that only a small number of harmonics are required to synthesize either smoothed triangular or ramp waveforms. In addition, a third advantage is that the amplitudes and phases of the component sine waves can be tuned to compensate for large non-uniformities in the amplitude and phase responses of tunable filter.

With respect to FIG. 17, the outputs of two phase-locked digital-direct synthesis (DDS) sine wave generators are summed and amplified to form the drive waveform of the piezo-actuator. The phases and amplitudes of the DDS generators are adjusted to obtain the maximum duty cycle and linearity of the portion of the drive waveform during which the interferometric signals are sampled.

Figure 18:
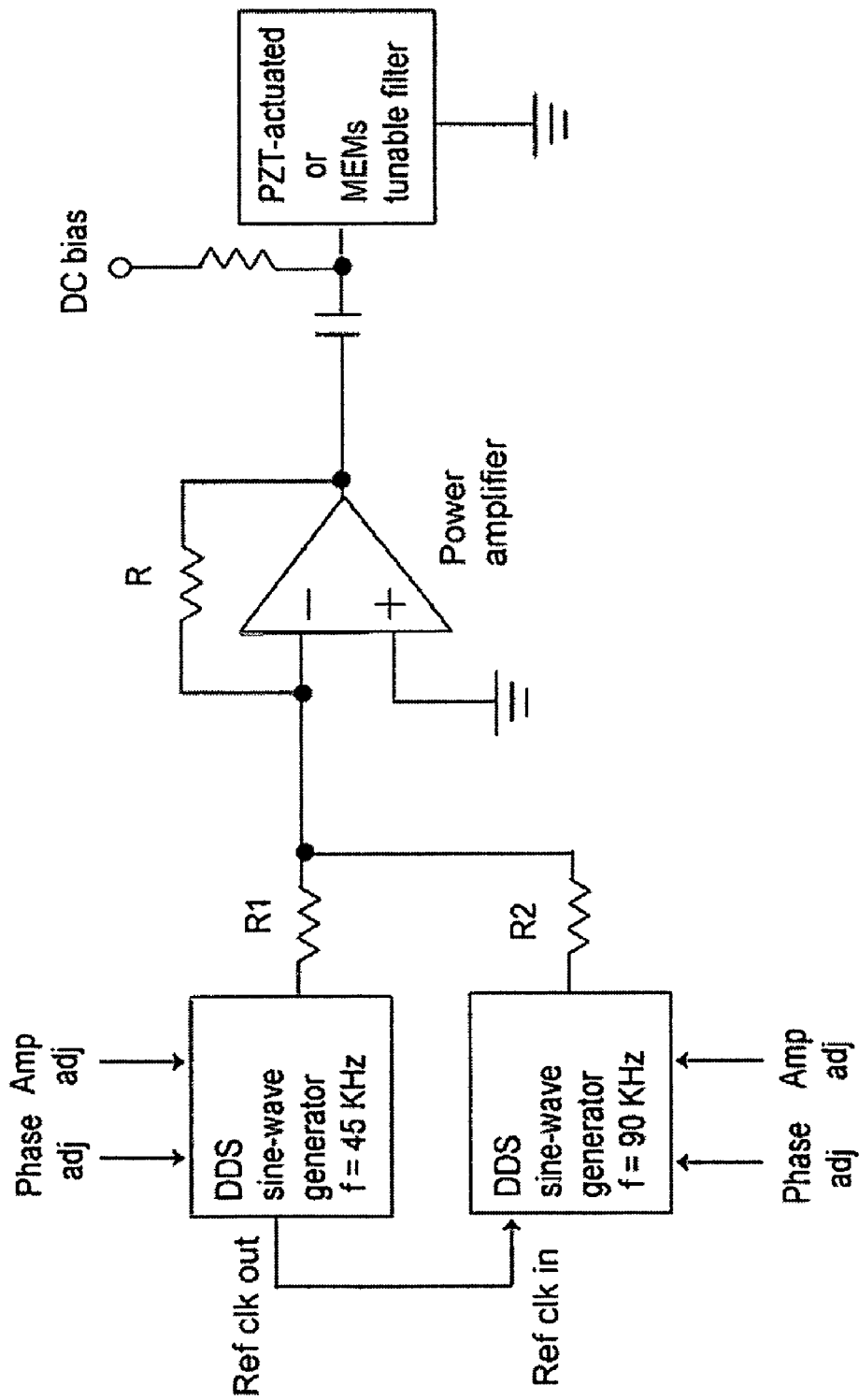
FIG. 18 shows a specific embodiment of a tunable-filter linearizing circuit based according to an illustrative embodiment of the invention.

A specific embodiment of a tunable-filter linearizing circuit based on two phase-locked digital direct synthesis (DDS) sine-wave generators is shown in FIG. 18. The circuit is designed to generate smoothed ramp displacement of a piezo-actuated Fabry-Perot filter with the frequency response shown in FIG. 15. The primary excitation frequency of the filter (about 45 KHz), which sets the repetition rate of the laser, is typically selected such that both this frequency and its second harmonic (about 90 KHz) are located outside of the major resonant peaks of the filter response. In practice, the relative amplitudes of the about 45 KHz and about 90 KHz sine waves are adjusted to obtain the narrowest range of clock frequencies during the falling portion of the drive waveform.

This tuning process can be performed in real time with an oscilloscope set to display the gated Fourier transform of the clock signal. Test results demonstrate that, compared to the conventional sinusoidal drive waveform, the dual-sinusoidal harmonic drive waveform reduces the maximum clock frequency by about 30% and clock frequency span by a factor of 3, while maintaining the same about 100 nm sweep range. These improvements increase the signal to noise ratio of the system and reduce certain artifacts.

It should be appreciated that various aspects of the claimed invention are directed to subsets and substeps of the techniques disclosed herein. Further, the terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed. Accordingly, what is desired to be secured by Letters Patent is the invention as defined and differentiated in the following claims, including all equivalents.

The invention claimed is:

1. An optical coherence tomography data collection apparatus, the apparatus comprising
   a first gain element;
   a second gain element, each gain element having a different gain dependence on polarization; and
   a Fourier-domain mode-locked laser defining a cavity, the laser comprising
      a frequency tuning element in optical communication with the first gain element, the first gain element disposed within the laser cavity;
   the second gain element disposed outside the cavity,
   wherein the gain dependence on polarization of the first gain element is less than the gain dependence on polarization of the second gain element.

2. The optical coherence tomography data collection apparatus of claim 1, wherein the apparatus further comprises
   a sample clock generator configured to clock an analog-to-digital converter, the analog-to-digital converter configured to sample interference signals at an output of a main interferometer; and
   a digital control system configured to stabilize a drive frequency of the frequency tuning element of the Fourier-domain mode-locked laser using at least one control signal derived from the sample clock generator.

3. The apparatus of claim 1 wherein the Fourier-domain mode-locked laser further comprises an optical delay element that comprises a pair of fiber coils whose relative orientations are adjusted to reduce the effects of polarization mode dispersion.

4. The apparatus of claim 2 wherein the sample clock generator further comprises an element selected from the group consisting of: a sample clock interferometer, a photo-receiver, an automatic gain control amplifier, a frequency multiplier, a zero-crossing detector, and a clock switch.

5. The apparatus of claim 2 wherein the sample clock generator further comprises an element selected from the group consisting of: a Mach-Zehnder interferometer comprising a pair of 2×2 fiber coupler, a Michelson interferometer with mismatched lengths in sample and reference arms, a common-path Michelson interferometer including an element with two partially reflective interfaces and a Fabry-Perot interferometer.

6. The apparatus of claim 2 wherein the sample clock generator further comprises an analog multiplier, the analog multiplier configured to perform a squaring function on an input interference signal.

7. The apparatus of claim 2 wherein the sample clock generator further comprises an analog multiplier for the multiplication of a pair of signals derived from an interference signal transmitted through a phase-shifting RF power splitter.

8. The apparatus of claim 2 wherein the sample clock generator further comprises: an exclusive OR gate for the transmission of a pair of phase-shifted pulse trains, the pulse trains derived from a zero-crossing detector applied to an interference signal and a delayed replica of the zero-crossing detector's output.

9. The apparatus of claim 2 wherein the sample clock generator further comprises an exclusive OR gate for the transmission of a pair of phase-shifted pulse trains, wherein the pulse trains are derived from a pair of zero-crossing detectors applied to sinusoidal signals derived from a phase-shifting power splitter.

10. The apparatus of claim 2 wherein the sample clock interferometer generates phase-shifted interference signals for frequency modulation from a combination of a 2 ×2 coupler and an 3×3 coupler, the power splitting ratio of the 3×3 coupler chosen to obtain a pair of interference signals whose phases differ by approximately 90 degrees.

11. The apparatus of claim 2, wherein the apparatus further comprises a 4×4 coupler, the 4×4 coupler generating a pair of balanced signals with a quadrature phase relationship, the sample clock generator generating a single ADC clock signal.

12. The apparatus of claim 2 wherein the sample clock generator generates complex-valued signals for Fourier transformation by recording OCT data using a pair of ADC clock signals whose phases differ by 90 degrees.

13. An optical coherence tomography data collection apparatus, the apparatus comprising
   a first gain element;
   a second gain element, each gain element having a different gain dependence on polarization; and a laser defining a cavity, the laser comprising
  a frequency tuning element in optical communication with the first gain element, the first gain element disposed within the laser cavity;
the second gain element disposed outside the cavity,
wherein the gain dependence on polarization of the first gain element is less than the gain dependence on polarization of the second gain element.

14. The apparatus of claim 13, wherein the apparatus further comprises
  a sample clock generator configured to clock an analog-to-digital converter, the analog-to-digital converter configured to sample interference signals at an output of a main interferometer; and
  a digital control system configured to stabilize a drive frequency of the frequency tuning element of the laser using at least one control signal derived from the sample clock generator.

15. The apparatus of claim 13 wherein the laser further comprises an optical delay element that comprises a pair of fiber coils whose relative orientations are adjusted to reduce the effects of polarization mode dispersion.

16. The apparatus of claim 14 wherein the sample clock generator further comprises an element selected from the group consisting of: a sample-clock interferometer, a photoreceiver, an automatic gain control amplifier, a frequency multiplier, a zero-crossing detector, and a clock switch.

17. The apparatus of claim 14 wherein the sample clock generator further comprises an element selected from the group consisting of: a Mach-Zehnder interferometer comprising a pair of 2×2 fiber coupler, a Michelson interferometer with mismatched lengths in sample and reference arms, a common-path Michelson interferometer including an element with two partially reflective interfaces and a Fabry-Perot interferometer.

18. The apparatus of claim 14 wherein the sample clock generator further comprises an analog multiplier, the analog multiplier configured to perform a squaring function on an input interference signal.

19. The apparatus of claim 14 wherein the sample clock generator further comprises an analog multiplier for the multiplication of a pair of signals derived from an interference signal transmitted through a phase-shifting RF power splitter.

20. The apparatus of claim 14 wherein the sample clock generator further comprises: an exclusive OR gate for the transmission of a pair of phase-shifted pulse trains, the pulse trains derived from a zero-crossing detector applied to an interference signal and a delayed replica of the zero-crossing detector's output.

21. The apparatus of claim 14 wherein the sample clock generator further comprises an exclusive OR gate for the transmission of a pair of phase-shifted pulse trains, wherein the pulse trains are derived from a pair of zero-crossing detectors applied to sinusoidal signals derived from a phase-shifting power splitter.

* * * * *